US007452326B2

(12) United States Patent
Fladl et al.

(10) Patent No.: US 7,452,326 B2
(45) Date of Patent: Nov. 18, 2008

(54) USER-FRIENDLY VIBROSTIMULATION DEVICE

(75) Inventors: Theresia (Thevan) Fladl, Vancouver (CA); Brian Keane, Vancouver (CA); Thomas (Llyod) Bellaire, Burnaby (CA); Daniel Leland, Coquitlam (CA); Ernest Janzen, North Vancouver (CA)

(73) Assignee: British Columbia Institute of British Columbia, Burnaby, BC (CA)

( * ) Notice: Subject to any disclaimer, the term of this patent is extended or adjusted under 35 U.S.C. 154(b) by 214 days.

(21) Appl. No.: 11/580,081

(22) Filed: Oct. 13, 2006

(65) Prior Publication Data

US 2008/0139980 A1 Jun. 12, 2008

(51) Int. Cl.
*A61F 5/00* (2006.01)

(52) U.S. Cl. .......................................... 600/38; 601/46

(58) Field of Classification Search ............. 600/38–41; 601/46–83

See application file for complete search history.

(56) References Cited

U.S. PATENT DOCUMENTS 3,856,002 A 12/1974 Matsumoto
4,002,164 A 1/1977 Bradley
6,991,599 B2 1/2006 Hudson
2004/0193080 A1 9/2004 Siddhartha

FOREIGN PATENT DOCUMENTS

WO WO 03/003967 1/2003

*Primary Examiner*—John P Lacyk
(74) *Attorney, Agent, or Firm*—Fasken Martineau DuMoulin LLP

(57) ABSTRACT

A vibrostimulation device for slidingly communicating with tactile receptors in a human body. The device comprises an elongate vibrator module and a handle component configured for releasably engaging and rotationally communicating with the vibrator module. The vibrator module comprises a vibrating end portion containing therein an electrically controllable vibratory apparatus interconnected by a resilient shock-absorbing coupler to a power supply module. The resilient shock-absorbing coupler is configured to extend the vibrating portion away from the power supply module at an acute angle. The handle component comprises a base portion configured for releasably engaging and rotationally cooperating with the power supply module of the vibrator module, a vertical member pivotably cooperating with the base portion, and a cantilevered upper portion extending outward from the vertical portion. The upper handle portion is provided with a switching device that cooperates with the base handle portion for electrically controlling the vibrator module.

30 Claims, 20 Drawing Sheets

(b)

(b)

(b)

USER-FRIENDLY VIBROSTIMULATION DEVICE

FIELD OF THE INVENTION

This invention relates to vibrostimulation devices. More particularly, this invention relates to vibrostimulation devices that are easily operable and manipulable by individuals with impaired motor skills and/or impaired perception of tactile stimuli.

BACKGROUND OF THE INVENTION

The human body is equipped with receptors integrally connected to and cooperating with the central nervous system, to sense, process and interact with five general types of external environmental stimuli which include sight, smell, taste, sound, and touch. The sensory receptors signal changes in: (a) the environment, or (b) in the human body relative to the environment, and relay this information to the central nervous system. External tactile environmental stimuli are detected and monitored by a class of receptors called exteroreceptors.

Skin contains a variety of exteroceptors distributed throughout the epidermal, dermal and subcutaneous layers of cells. Each type of exteroceptor is specialized to detect only one specific stimulus e.g., heat or cold (i.e. thermoreceptors), pain (i.e. nociceptors), and tactile stimuli such as touch and pressure (i.e. mechanoreceptors). Nociceptors are primarily comprised of nerve endings distributed throughout the body, and are especially prevalent in the dermal and subcutaneous layers of cells. Mechanoreceptors are distributed throughout the epidermal, dermal and subcutaneous layers of cells. Delicate intermittent tactile stimuli applied to the hands and face can be precisely sensed and localized by phasic receptors such as hair follicles and Meissner's corpuscles distributed throughout the epidermal and dermal cell layers, while constant but very light cutaneous stimuli are detected by tonic receptors such as Ruffini endings and Merkel cells, also primarily located in the epidermal and dermal layers. These specific types of exteroceptors are intimately involved in the body's ability to sense and organize a dynamic topographical map of tactile stimuli based on the plurality of signals transmitted to the brain from the individual exteroceptors. The communication and cooperation between the exteroreceptors and the central nervous system enable and precisely control manual dexterity, the ability to precisely and delicately manipulate objects, and the abilities to sense and respond to pleasant and pleasurable tactile stimuli. Pacinian corpuscles are deep-phasic pressure-sensitive receptors that are primarily distributed throughout the subcutaneous regions of the body and function primarily to sense significant squeezing and pressing forces. These types of forces are also sensed by nociceptors, but tend to mask and overwhelm the function of phasic and tonic exteroceptors located in the epidermal and dermal cell layers. The Pacinian corpuscles are also responsible for modulating responses related to the regulation of grasping and gripping, but do not significantly assist in the body's fine motor skill responses required for precisely controlled manual dexterity.

Many people experience as a result of traumatic injuries or degenerative diseases, permanent damage to the central nervous system and/or to the spinal chord and/or to exteroreceptors, particularly the phasic and tonic receptors, thereby resulting in significant and permanent losses of tactile sensory perception within their extremities and body trunk regions, and also, in nerve-mediated fine motor control over the precise movement and control of their extremities. However, although their abilities to receive and process tactile stimuli and to control their body movements in response thereto have been impaired to some significant degree, people suffering such impairments are not often impaired in their abilities to sense, process and positively experience visual, auditory, olfactory and oral stimuli. Moreover, a significant portion of such people have functional nocireceptors and deep-phasic receptors that communicate and cooperate with some portions of the central nervous system, and thereby are capable of at least some degree of gross motor control of functions such as grasping and gripping. Furthermore, persons with physical disabilities typically retain full organ function as well as their intellectual and emotional functionality and qualities, and therefore, retain their needs and desires to experience and respond to such non-tactile stimuli in a physical manner. Examples of such experiences and responses include sexual pleasure and gratification.

Devices and appliances employable for sexual pleasure and gratification are well known in the prior art and are widely available to the general public. They include simple phallus-shaped structures provided with vibrator motors housed therein as exemplified in U.S. Pat. No. 5,573,499, for external and internal stimulation of body surfaces. The options available with such simple appliances are expandable by the use of couplings to interconnect the devices with handles or other such devices, as disclosed in published U.S. patent application Ser. No. 10/395,863. Other types of devices and appliances such as those described in U.S. Pat. No. 5,690,603, U.S. Pat. No. 5,853,362 and published U.S. patent application Ser. No. 10/797,634 have been ergonomically designed for ease of graspability and manoeuvrability to facilitate internal stimulation of certain organs and/or to enable concurrent use with a partner. However, such devices and appliances tend to be useful primarily for stimulation of phasic and tonic exteroreceptors that are situated in the epidermal and dermal layers immediately underlying internal and external body surfaces. Furthermore, their structural designs and operational controls typically require some degree of manual dexterity combined with muscular agility and fine motor control over body extremities. Accordingly, such devices and appliances are not particularly useful or satisfactory for focused stimulation of the deep-phasic pressure-sensitive receptors such as Pacinian corpuscles that are primarily distributed throughout the subcutaneous regions of the body.

More elaborate configurations of sex aid devices and appliances requiring less manual dexterity and less manipulation by hand are also known in the prior art. For example, U.S. Pat. No. 6,890,293 teaches a driving apparatus for a massaging device for sexual organs that is mountable on a pedestal. Published U.S. patent application Ser. No. 10/786,268 discloses a bicycle handle bar type apparatus which is interconnectible with a U-shaped intermediate component to a detachable dildo. The opposing ends of the handle bar apparatus are simultaneously grippable with two hands to enable easier manipulation of a dildo interconnected thereto. U.S. Pat. No. 6,540,667 describes a device comprising two elongate members secured by a pivotal connection whereto a sexual appliance is removably attached. The device is provided with a biasing member to bias apart the opposite ends of the two elongate members. The sexual appliance can be made to travel back and forth along a longitudinal axis by compressing and uncompressing the two elongate members with the legs of an operator. U.S. Pat. No. 6,899,671 describes a three-arm Y-shaped tubular apparatus wherein the outer arms are secured to a user's ankles by cuffs, and a sexual appliance is detachably engaged with the centre arm. The apparatus is then operated in a hands-free manner by rhythmic rocking of the user's hips. Although such elaborate devices may not require significant hand manipulation when in use, their assembly, preparation for use, and disassembly requires significant manual dexterity and fine motor skill control. Consequently, such devices and appliances are difficult to handle and frustrating to use by persons with impaired motor skills.

SUMMARY OF THE INVENTION

The exemplary embodiments of the present invention, at least in preferred forms, are directed to vibrostimulation devices that are easily operable and manipulable and additionally, are useful for communicating with deep-phasic exteroreceptors.

According to one preferred embodiment of the invention, there is provided a vibrostimulation device comprising a vibrator module, a power supply module, a resilient shock-asbsorbing coupler for interconnecting the vibrator module and the power supply module, a handle component for releasably engaging and rotationally communicating with the power supply module, and a switching device for electrically controlling the vibrator module. The vibrator module is provided with at least one motor for producing therein and therefrom strong vibrations. The resilient shock-absorbing coupler is configured for dampening the vibrations generated by the vibrator module and for limiting transmission of said vibrations to the power supply module. The power module is preferably adaptable for cooperation with a rechargeable battery pack. Alternatively, the power module may be configured for cooperation with disposable batteries. The power supply module is provided with an end component having at least one pair of spaced apart ribs for securely engaging therewith the handle component whereby the handle component extends upward from the power supply module and is generally cantilevered away from the vibrator module interconnected with the power supply module. The handle component is provided with a receptacle for engaging therein the switching device. The switching device is configured to turn on and off the motor(s) provided therein the vibration module and to control the intensity, the magnitude and the motions of the vibrations produced therein and therefrom the vibrator module.

According to one preferred aspect, the vibrator module comprises a vibrating end portion interconnected to a power supply module by a shock-absorbing coupler. The vibrating end portion comprises a hollow elongate cylindrical housing containing therein at least one motor for producing therewith transmittable vibrations. One end of the vibrating end portion is configured to interconnect with the coupler and the power supply module, while the opposite end is closed with a domed cap region forming an integral extension therefrom the cylindrical housing. The outside diameter of the housing and the materials used to construct the housing, are selected for their suitability for insertion into body orifices. The vibrations produced by the motor contained therein the vibrator module may be a single repeating motion. It is important that the intensity and the magnitude of the vibrations produced are sufficient to stimulate the deep-phasic exteroreceptors.

According to another preferred aspect, the vibrating end portion is configured as an elongate truncated cone. The truncated distal end of the conical vibrating end portion depends backward toward the proximal end of the vibrating end portion. It is preferred that the truncated distal end is provided with a concave surface therein. In a preferred form, an elongate rib is provided along the longitudinal axis of the elongate truncated cone-shaped vibrating end portion. It is preferred that the elongate rib depends from and extends outward from the proximal end of the vibrating end portion to conjoin the truncated distal end thereby providing an anvil-shaped profile to the distal end 120. The elongate rib is preferably conjoined to the vibrating end portion by opposing concave surfaces. The vibrating end portion may optionally be configured as an elongate truncated cylinder.

According to yet another preferred aspect, the power supply module comprises an elongate housing for containing therein a rechargeable battery pack. One end of the housing is configured to cooperate with the coupler and the interconnecting end of the vibrator module, and to supply power therethrough to the vibrator module. The opposite end of the power supply housing is a concave base and is provided with a receptacle in the centre of said concave base for receiving therein and cooperating therewith an electrical jack from a charging device for recharging the battery pack as required. The concave base acts as a funnel for the jack, freeing the user of the need to target a small opening using fine motor adjustments. The outer surface of the power supply housing is provided with at least one pair of spaced apart ribs extending therefrom along the longitudinal axis for securely engaging therewith the handle component.

According to a further preferred aspect, the coupler generally comprises a truncated cylinder with the opposing ends configured to extend the vibrating end portion away from the power supply module at an acute angle. It is preferred that the coupler comprises a resilient shock-absorbing material.

According to another preferred aspect of the present invention, the handle component comprises a generally L-shaped element having a somewhat palm-shaped curvilinear top surface cantilevering from a vertical member that extends upward from an elongate flat base provided with opposing flanges extending downward at least partially along the longitudinal axis of the base. The height and girth of the vertical member are configured to enable secure gripping by hand with minimal manual dexterity and motor control skills. The dimensions and topography of the curvilinear top surface are configured to also enable secure gripping by hand with minimal manual dexterity and motor control skills. The curvilinear top surface is preferably provided with a receptacle for engaging therein a switching device for electrically controlling the vibrator module. The opposing flanges extending downward from the elongate flat base are configured to demountably engage the ribs protruding therefrom the power supply module housing thereby securely interconnecting the handle component with the power supply module. When the vibrator module is interconnected and coupled with the power supply module, the handle component may be engaged with the power supply module such that the distal end of the curvilinear top surface of the handle is pointing in the same direction as the domed end of the vibrator module.

According to another preferred aspect of the present invention, the handle component is provided with a pivotably connected base component that is configured to releasingly engage and rotationally communicate with the power supply module such that orientation of the distal end of the vibrating end portion of the vibrator module can be changed from a generally upward to a generally sideway to a generally downward pointing orientation relative to the curvilinear top surface of the handle module.

In a yet further preferred form, the curvilinear top surface of the handle component may be provided with an integral toroidal loop portion extending underneath and in parallel with the top surface from its distal end to an interconnecting juncture with the vertical member thereby forming an aperture through which a hand may be inserted and securely grip said loop portion for increased ease and comfort of handling and manipulation of the vibrostimulation device of the present invention thereby enhancing satisfactory operation of the device with minimal requirements for manual dexterity and motor control capability.

In yet a further preferred form, the vertical member of the handle component may comprise two interconnecting elements provided with means for adjusting and securing the orientation and positioning of the curvilinear top surface relative to the elongate flat base of the handle component. In one example, the curvilinear top surface may be adjusted upward thereby moving the top surface toward a more vertical orientation relative to the vibrator module, or alternatively, if the curvilinear top surface is adjusted downward, it will move toward a more horizontal orientation relative to the vibrator module. In another example, the curvilinear top surface may be swivelled to the left or the right around a vertical axis thereby moving the handle component into an offset position relative to the vibrator module.

In a preferred form, a switching device is provided for controlling the motor(s) contained within the vibrator module. The switching device comprises a housing wherein a plurality of large buttons cooperate with dedicated switches to turn the motor on and off, and to control the reciprocating and/or oscillating motions of the vibrations produced therein. Each switch is activated and deactivated by simply pressing the button connected thereto with a finger, a knuckle, a wrist or a palm or alternatively, by pushing the button against an inanimate object by manipulating the housing. The housing is configured to fit within the handle component and to be operated in cooperation with the handle.

According to another preferred embodiment, there is provided a charging apparatus for cooperating with the vibrostimulation device of the present invention. The charging apparatus comprises a transformer that is demountably engagable with an electrical outlet, a male jack end for demountably engaging and cooperating with a charging receptacle of a rechargeable battery pack, and wiring interconnecting the transformer and the male jack end. The male jack end protrudes from a moulded housing comprising a pair of opposing paddles conjoined by a ribbed sheath encompassing the wiring connected to the male jack end, wherein the thickness of the sheath is greater than the thickness of the paddles. Consequently, one of the paddles will be somewhat elevated above the surface on which the charging apparatus is placed thereby facilitating the grasping and manipulating of the male jack end by individuals having impaired dexterity and motor control capabilities. The housing of the transformer is optionally configured to facilitate its grippability and manipulation by individuals having impaired dexterity and motor control capabilities. It should be noted that the housing is adaptable to a number of jack and cable designs for other products cooperating with rechargeable battery packs.

According to another preferred embodiment, there is provided a charging apparatus for cooperating with the vibrostimulation device of the present invention. The charging apparatus comprises a transformer that is demountably engagable with an electrical outlet, said transformer provided with an integral charging cradle for receiving therein and cooperating therewith the power supply module of vibrostimultation device of the present invention.

According to yet another preferred embodiment of the present invention, there is provided a kit of parts forming a vibrostimulation device that is easily manipulable, assembled and disassembled, and operable by individuals with impaired motor skills and/or impaired perception of tactile stimuli. Said kit is preferably provided with instructions for the assembly, operation, cleaning and care of the device as explained herein.

BRIEF DESCRIPTION OF THE DRAWINGS

The present invention will be described in conjunction with reference to the following drawings, in which:

FIG. 4*b* is a top view of the embodiment from FIG. 1 shown in operation;

FIG. 10(*b*) is a front perspective view of the sprocket barrel shown in FIG. 10(*a*);

FIG. 11(*b*) is a side view of the handle end cap structure from FIG. 11(*a*);

FIG. 18(*b*) is a cross-sectional view of the handle component from FIG. 14 showing the metal framework embedded in a compressible resilient material;

DETAILED DESCRIPTION OF THE INVENTION

The present invention provides vibrostimulation devices comprising a plurality of disengagible interlocking modules which individually and as an interlocked assembled whole, are manipulable and operable by individuals with impaired motor control of their extremities and/or impaired tactile sensory perception. The vibrostimulation devices of the present invention are additionally useful for communicating with deep-phase exteroreceptors located throughout the human body. The modules comprise at least one vibrator module configured to rotationally communicate with and releasably interlock with at least one handle component. The vibrator module comprises a vibrating end portion interconnected by a shock-absorbing coupler to a power supply module. The handle component is provided with means configured for demountable engagement and rotational communication with the power supply module. The handle component is provided with a switching device for electrically controlling the vibrator module, said handle component and switching device cooperating to concurrently releasably engage the vibrator module.

The power supply module may engage and cooperate with disposable batteries. Alternatively, the power supply module may be engagible with a rechargeable battery pack houseable within the power supply module. Vibrostimulation devices of the present invention provided with a power supply module comprising a rechargeable battery pack are preferably additionally provided with a disengagible charging module for recharging the battery pack.

The vibrostimulation devices of the present invention are optionally provided with easily graspable and manipulable attachments that slidingly cooperate with the vibrator module for refining and/or modulating and/or transmitting therefrom the vibrations produced therein. The vibrostimulation devices of the present invention are further optionally provided with easily graspable and manipulable sleeve attachments that slidingly and engagibly cooperate with the vibrator module to enable modification and refinement of the phallic profile of the vibrator module.

Exemplary embodiments of the vibrostimulation devices of the present invention are shown in the accompanying drawings, and are generally referred to by the numeral 10.

Figure 4A:
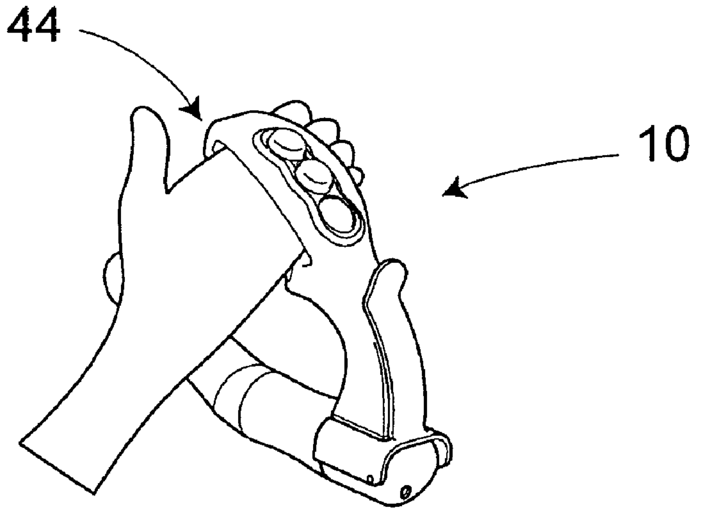
FIG. 4*a* is close-up perspective view showing engagement of a user's hand with the embodiment shown in FIG. 1.
Figure 4A:
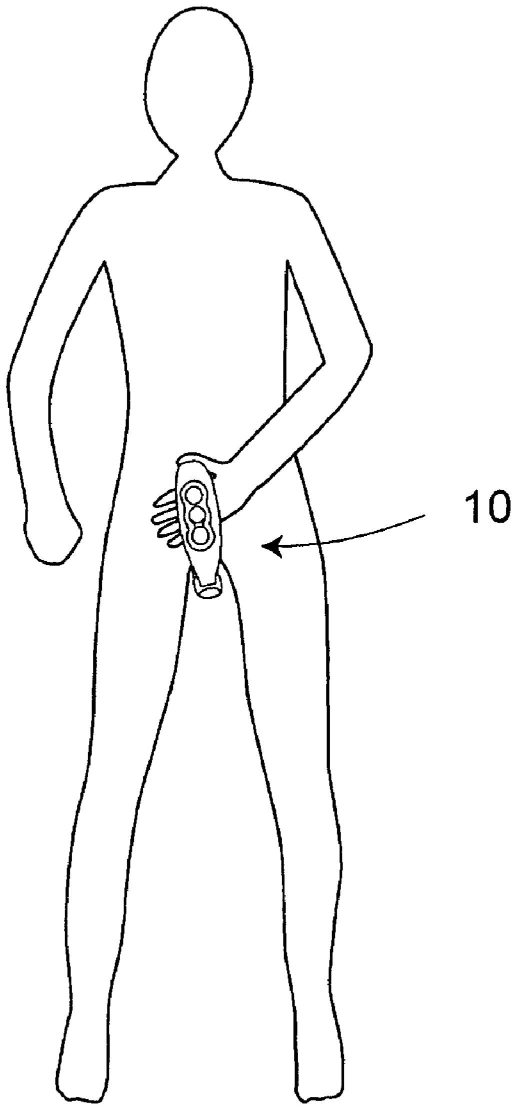
Figure 5:
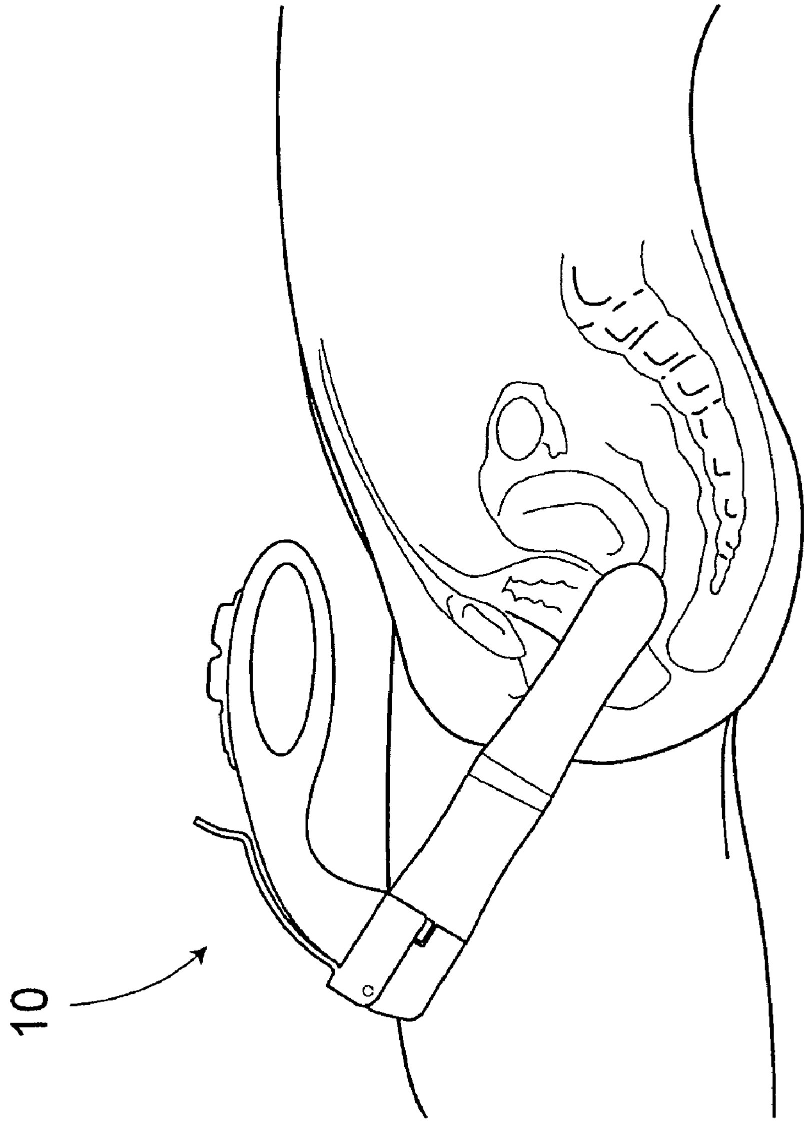
FIG. 5 is a sectional side view showing the embodiment from FIG. 1 in operation.
Figure 6:
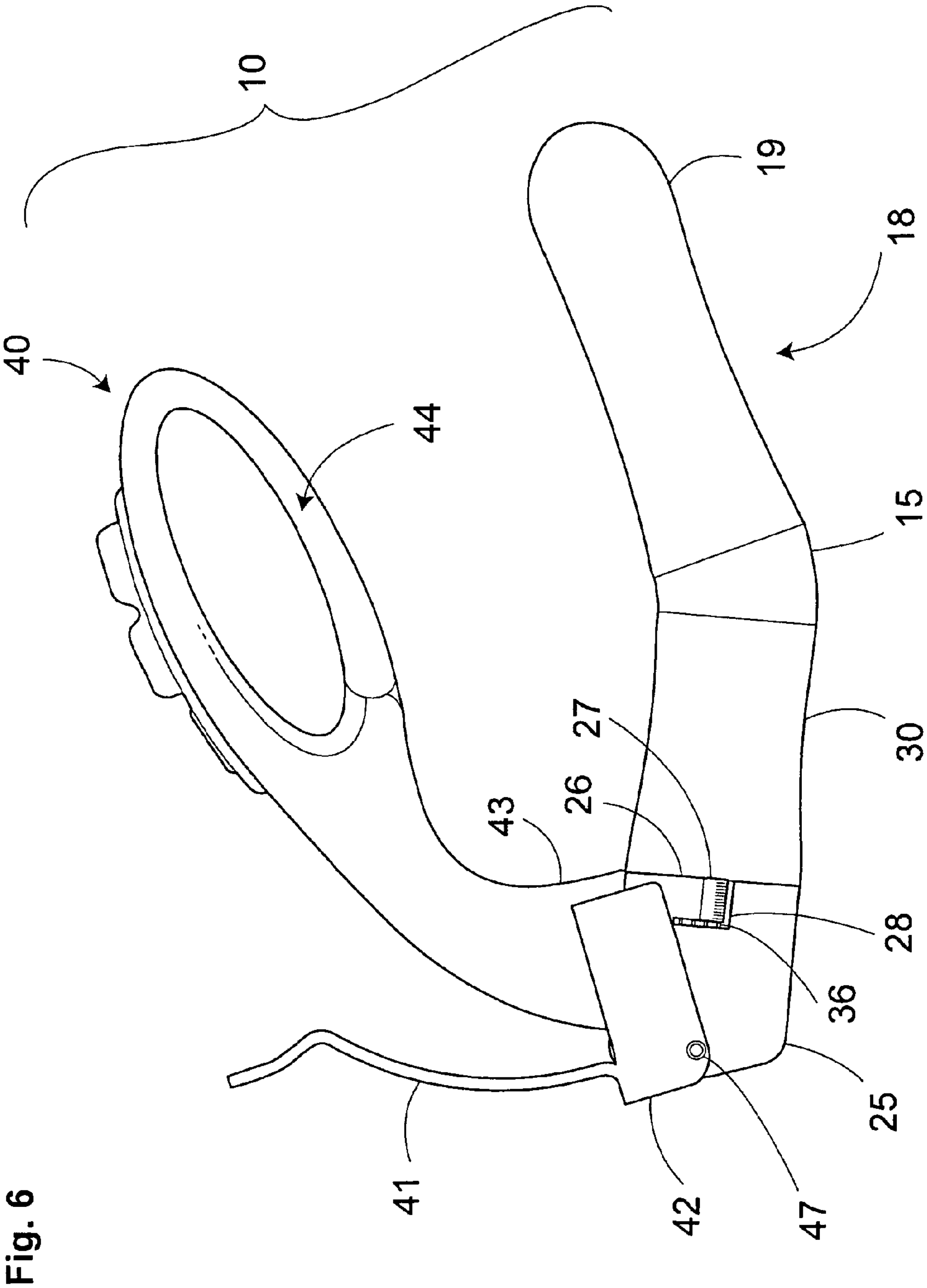
FIG. 6 is a side view of the embodiment from FIG. 1 wherein a locking device is shown in a disengaged position to enable rotatable reorientation of the dildo portion.
Figure 7:
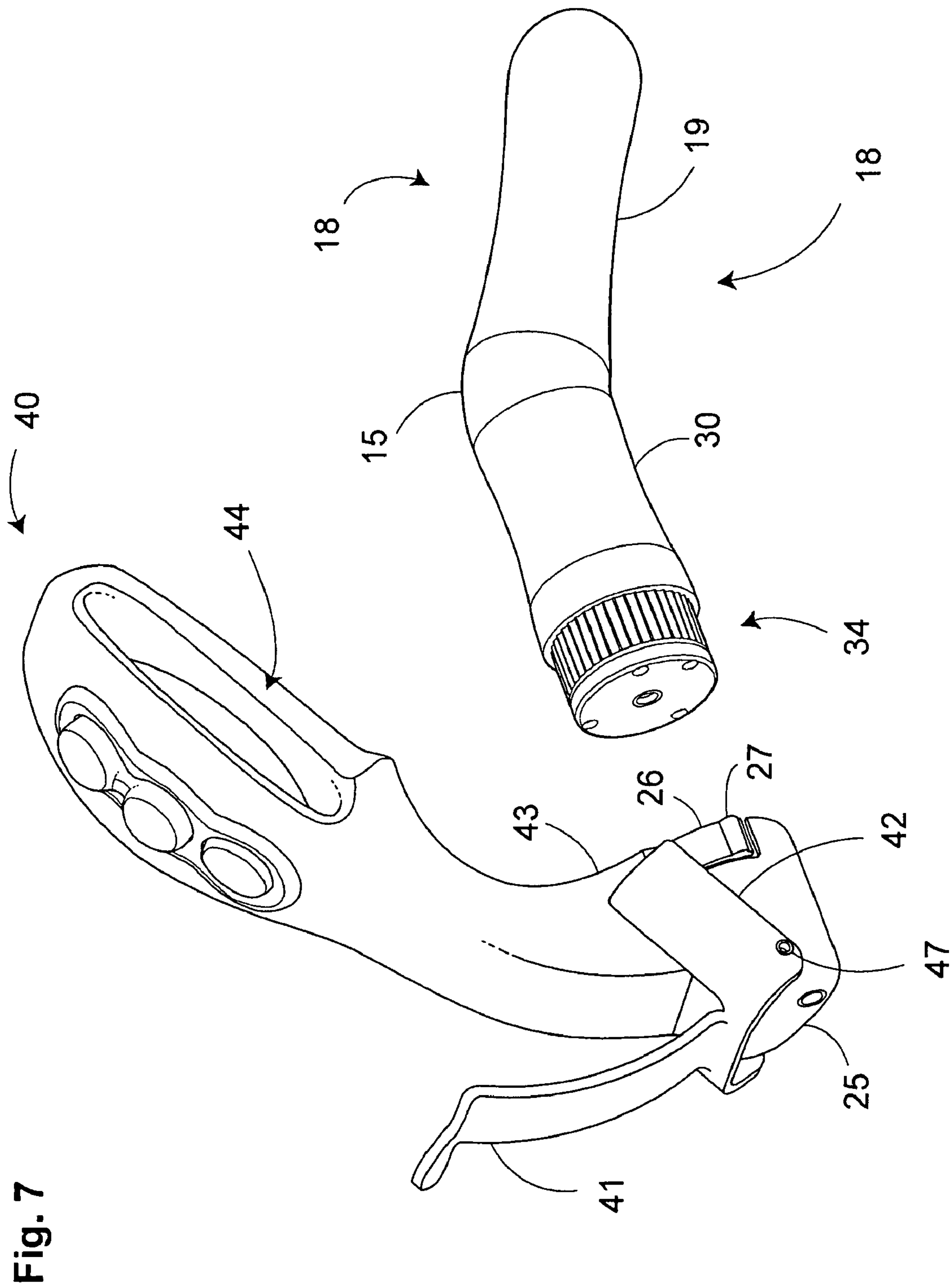
FIG. 7 is a side view of the embodiment from FIG. 1 showing the handle component separated from the vibrator module.

FIGS. 1-12 illustrate a preferred embodiment of the present invention configured for sliding communication about, with, and within body orifices. As can best be seen in FIGS. 1-3, the device 10 is provided with vibrator module 18 comprising a vibrating end portion 19 (i.e., the dildo end), a power supply module 30, a shock-absorbing coupler 15 interconnecting the vibrating dildo end 19 and the power supply module 30, a handle component 40 and a switching device 50. The proximal end of the dildo end 19 and the distal end of the power supply module 30 of the vibrator module 18, are interconnected by the shock-absorbing coupler 15. It is preferable that the configuration of the coupler 15 is in the form of a truncated cylinder wherein the opposing ends depend from each other at an acute angle. It is further preferable that the acute angle formed by the opposing ends of the coupler 15 is selected from the range of 5° to 65°, and most preferably from the range of 20° to 30°. It is within the scope of this invention to provide a coupler 15 having a linear longitundal axis or alternatively, the coupler 15 may be configured as an arcing cylinder. The handle component 40 comprises a handle end cap receptacle 25 configured to releasably engage the proximal end of the power supply module 30 opposite the distal end interconnected with the dildo 19, a generally upwardly extending vertical portion 43 from which extends a cantilevered top portion configured into a toroidal loop 44 at its distal end, and a locking device 41 configured for releasingly communicating with and engaging the vertical handle portion 43 as shown in FIGS. 6 and 7.

Figure 8:
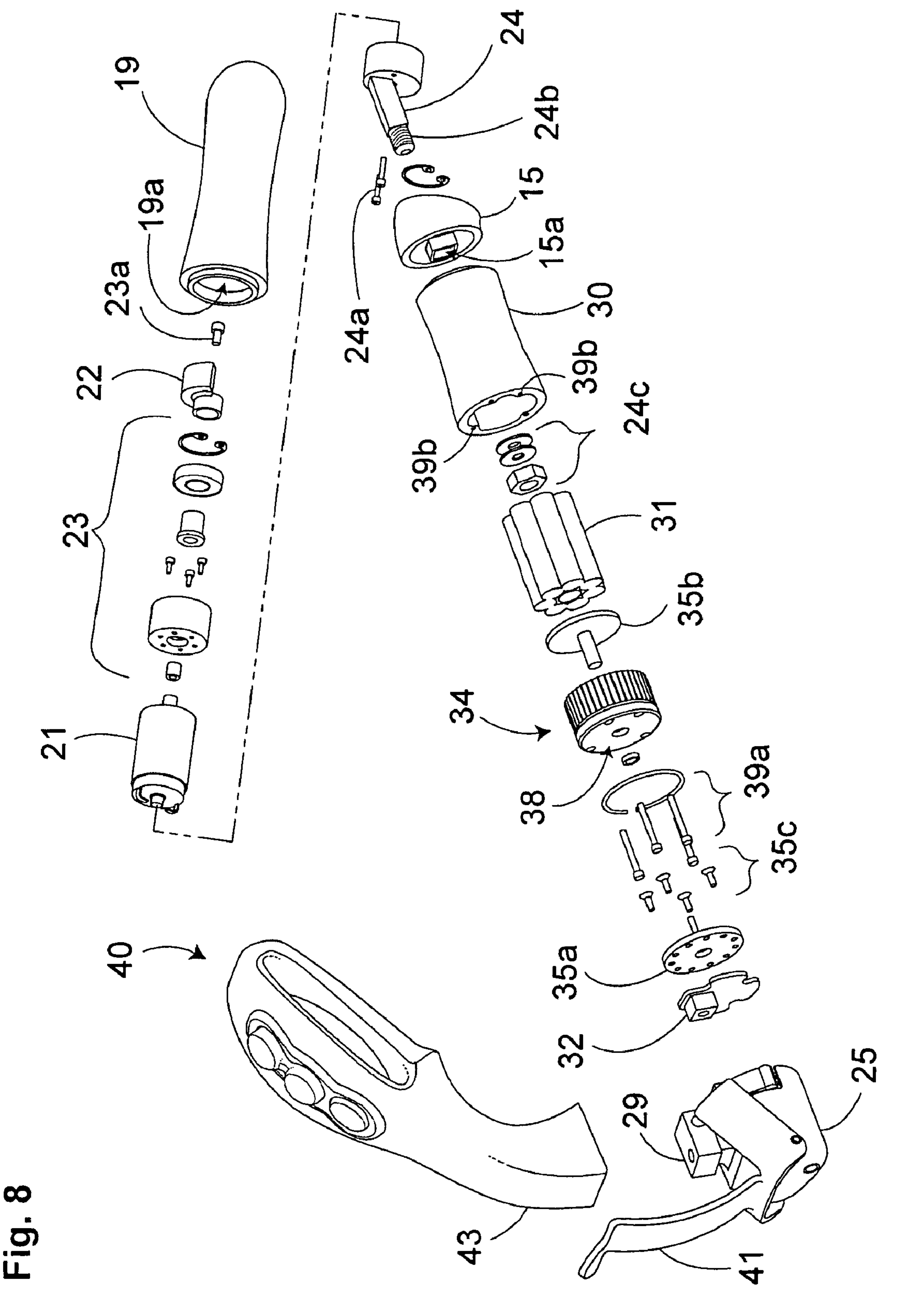
FIG. 8 is an exploded perspective view of the vibrator module of the embodiment shown in FIG. 1.
Figure 9:
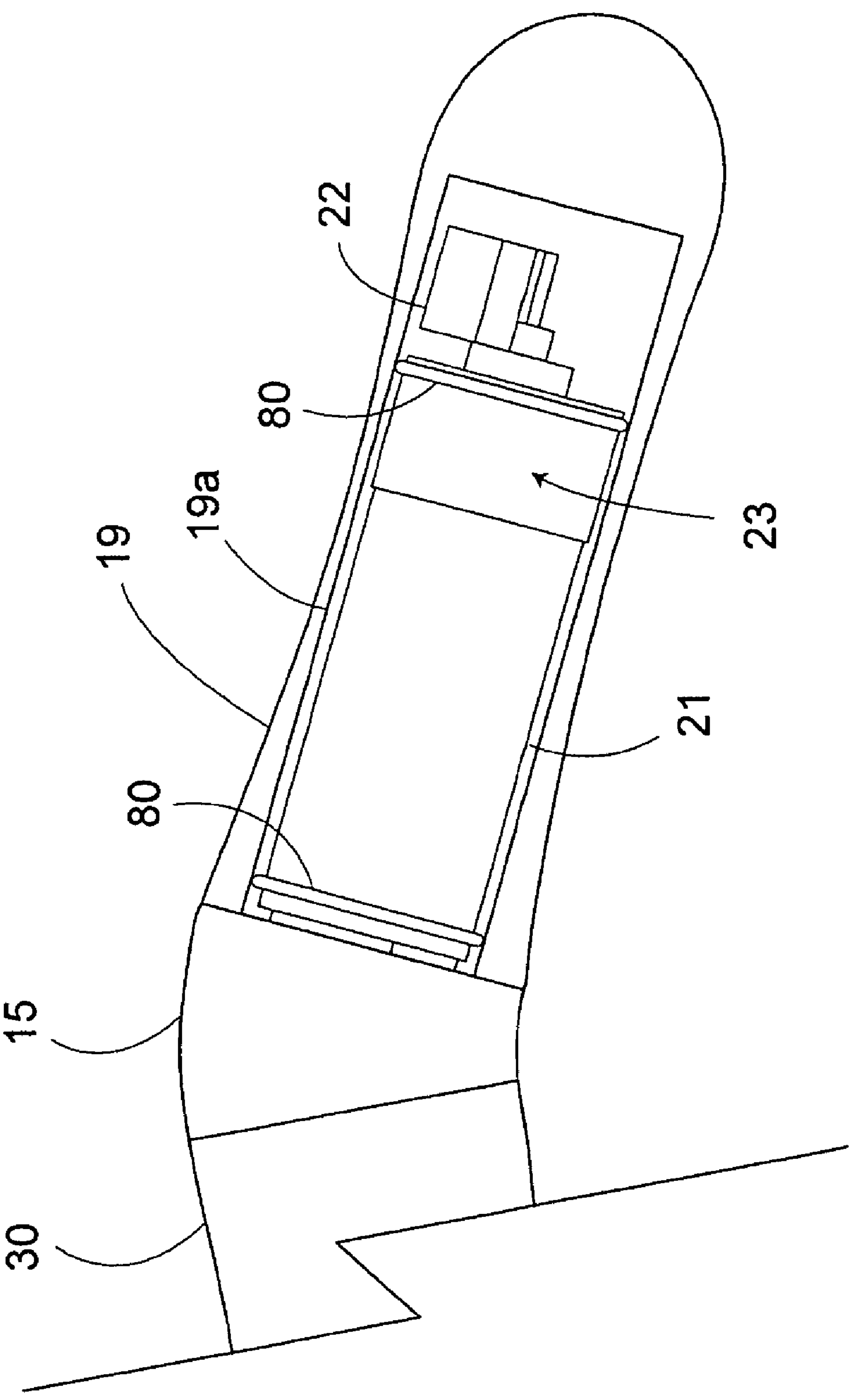
FIG. 9 is a cross-sectional view showing a preferred mounting configuration for the motor apparatus within the dildo portion of the embodiment shown in FIG. 1.
Figure 10A:
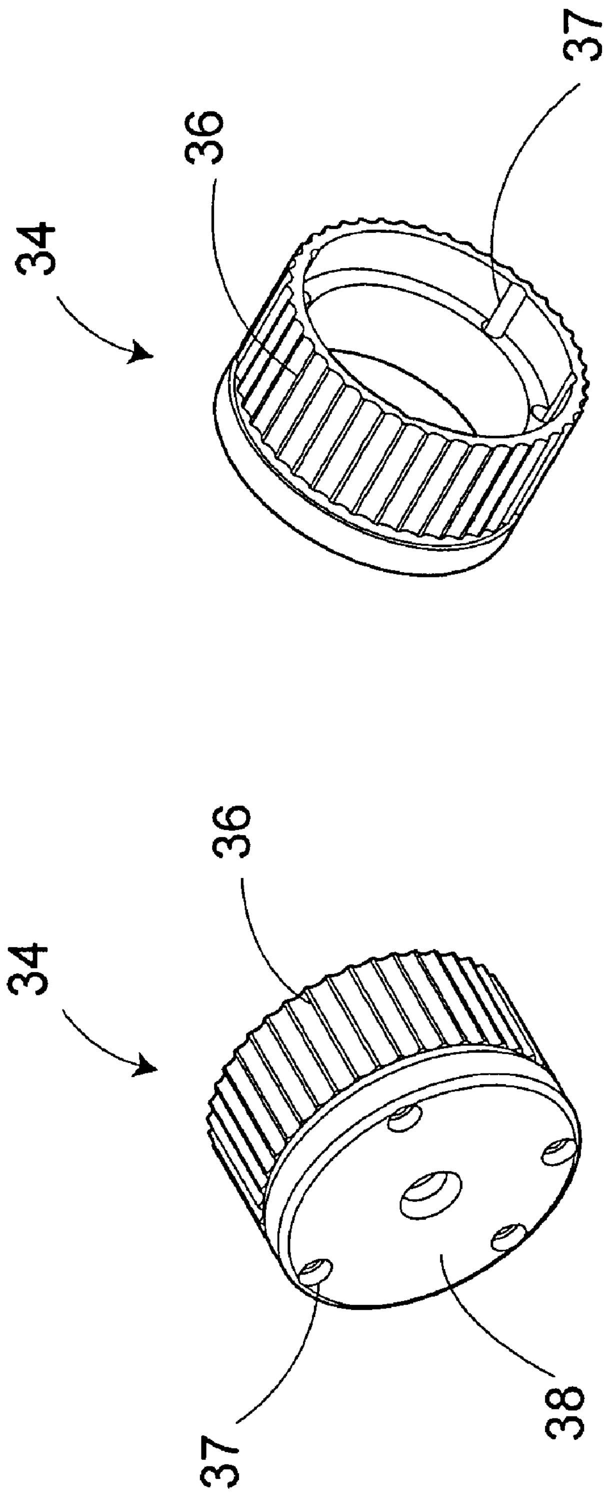
FIG. 10(*a*) is a rear perspective view of the sprocket barrel component of the power supply module shown in FIG. 8.
Figure 11A:
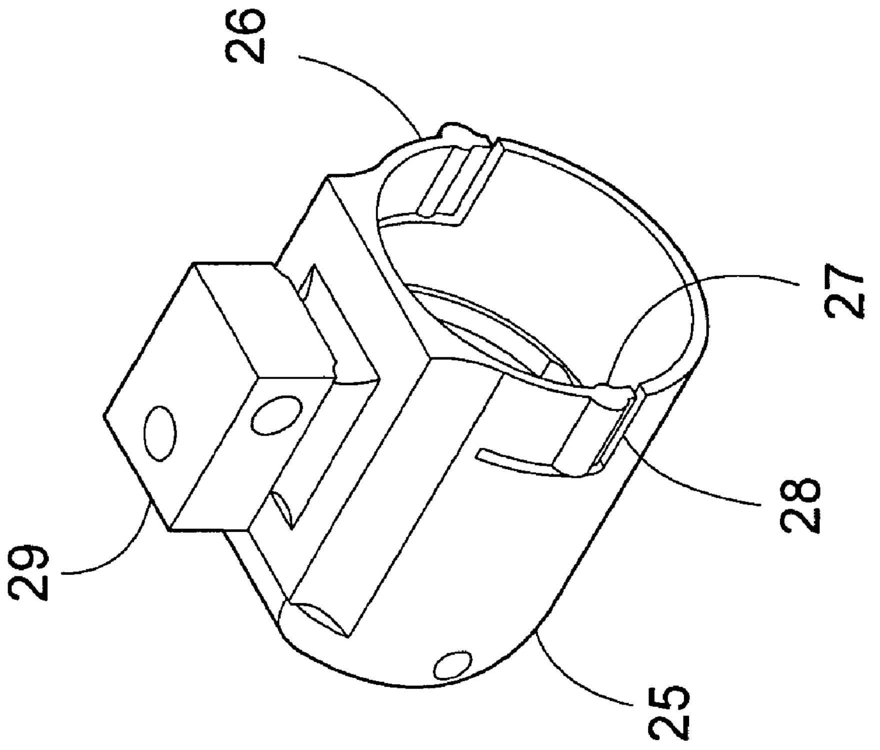
FIG. 11(*a*) is a front perspective view of the handle end cap structure of the embodiment from FIG. 1.
Figure 11A:
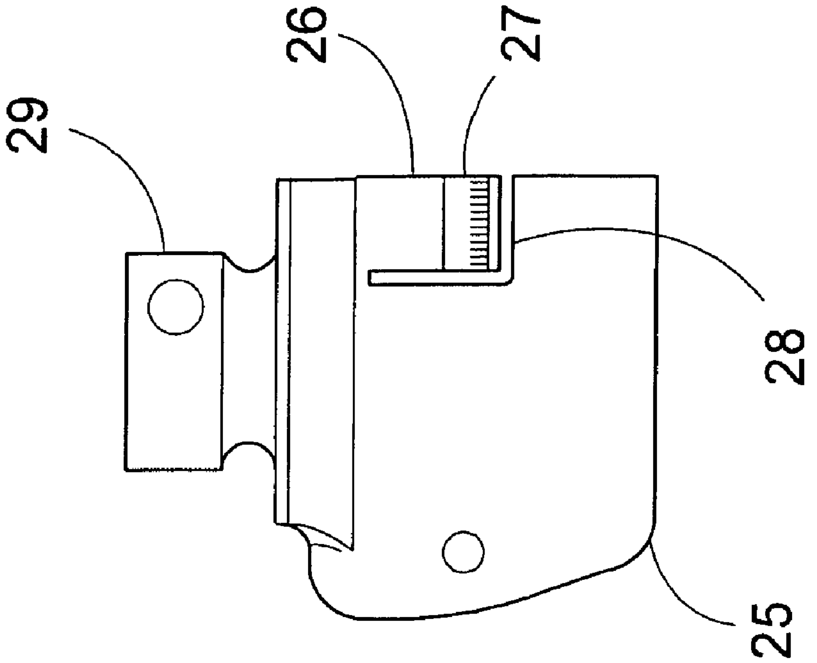

Exemplary embodiments of the vibrator module 18 are shown in FIGS. 8-10 wherein the dildo 19 is provided with a bore **19*a* extending inward from the proximal end of the dildo 19. The bore 19*a* is configured to receive and house therein a motor 21 that is engaged with and interconnected by a shaft assembly 23 to an eccentric weight 22 positioned toward the distal end of the dildo 19. The eccentric weight 22 is mounted to the shaft assembly 23 by a screw 23*a*. As shown in FIG. 9, a plurality of O-rings 80 may be optionally provided to encircle the motor 21 to separate the motor 21 from the bore 19*a* thereby significantly reducing heat transfer from the motor 21 to the dildo 19. Those skilled in this art will understand that additional cooperating motors may be provided within the vibrating end portion 19** for simultaneously producing multiple combinations of rotational, oscilating and reciprocating motions.

It should be noted that in the exemplary embodiment shown in FIGS. 1-12, the shock-absorbing coupler 15 is an arcing cylinder with its opposing ends truncated at an acute angle of about 25° C. The coupler 15 is provided with a slot **15*a* extending between the opposing ends for receiving therethrough a wiring conduit structure 24 that is secured to the dildo 19 with screws 24*a*. It is important to note that coupler 15 comprises a durable yet flexible and resilient moisture impenetrable material for concurrently sealably and compressingly engaging the vibrating end portion 19 and power supply module 30. The coupler 15 preferably comprises a shock-absorbing resilient material exemplified by rubber, polyurethane, polyurethane rubber, foamed polyurethane, flexible epoxy, elastomer and the like. The configuration and composition of the resilient shock-absorbing coupler prevents transmission of vibrations from the dildo end 19 to the power supply module 30 and handle component 40. These features enable sufficiently strong vibrations and vibratory motions to be generated therein the dildo end 19 for satisfactory communication with deep-phasic exteroreceptors such as Pacinian corpuscles, while insulating and protecting the power supply module 30 and handle component 40 from such vibrations and vibratory motions thereby significantly enhancing the ease of operating and maneuvering and the comfort of using the vibrostimulation device 10** by individuals with impaired motor controls and/or impaired tactile sensory perception.

The distal end of the power module 30 is configured to receive therethrough the threaded end portion **24*b* extending from the coupler 15. A nut and washer set 24*c* securely engages and locks together the power module 30 and shock-absorbing coupler 15. The power module 30 is configured to partially house a battery pack 31 so that the electrical discharge end of the battery pack communicates with the wiring conduit structure 24. The power module 30 is provided with a sprocketed barrel-shaped end cap structure 34 configured to house therein the portion of the battery pack 31 extending from the power module 30. The end cap structure 34 is securely mounted to the power module 30 by bolts 39*a* extending through bores 37 in the end wall 38 of the end cap structure 34, said bolts 39*a* cooperating with threaded bores 39*b* provided in the proximal end of the power module 30. An electrical contact plate 35*b* provided with an integral conduit extending therefrom, is interposed the battery pack 31 and the end wall 38 of the sprocket barrel end cap structure 34, said electrical contact plate 35***b* communicating therethrough said sprocket barrel end cap structure with a second electrical switching contact plate 35*a*.

As is best seen in FIGS. 6-8 and 11, the handle end cap structure 25 comprises a housing provided with a cylindrical inner bore configured to slidingly receive therein the sprocket barrel end cap structure 34 that is mounted to the proximal end of the power supply module 30. As shown in FIG. 8, a power jack receptacle 32 and an electrical switching contact plate 35*a* are interposed the handle end cap structure 25 and the sprocket barrel end cap structure 34. The sprocket barrel end cap structure receiving end of the handle end cap structure 25 is provided with a pair of opposed L-channels 28 that define a pair of inwardly-biasing arms 26, each arm 26 provided with a lobed end 27. A upper handle-engaging lug 29 is provided on the upper surface of the end cap structure 25 interposed the pair of inwardly biasing arms 26. As shown in FIG. 10, the outer surface of the sprocket barrel end cap structure 34 is preferably provided with a contiguous plurality of paired ribs 36 extending along the longitudinal axis of sprocket barrel end cap structure 34, said contiguous plurality of ribs 36 encircling the sprocket barrel end cap structure 34. When the sprocket barrel end cap structure 34 is inserted into the handle end cap structure 25, each lobed end 27 of each inwardly biasing arm 26 of the handle end cap structure 25 will communicate with and engage the space interposed two adjacent ribs 36 on the outer surface of the sprocket barrel end cap structure 34, thereby enabling precisely controllable rotation of the vibrator module 18 within the handle end cap structure 25.

Figure 2:
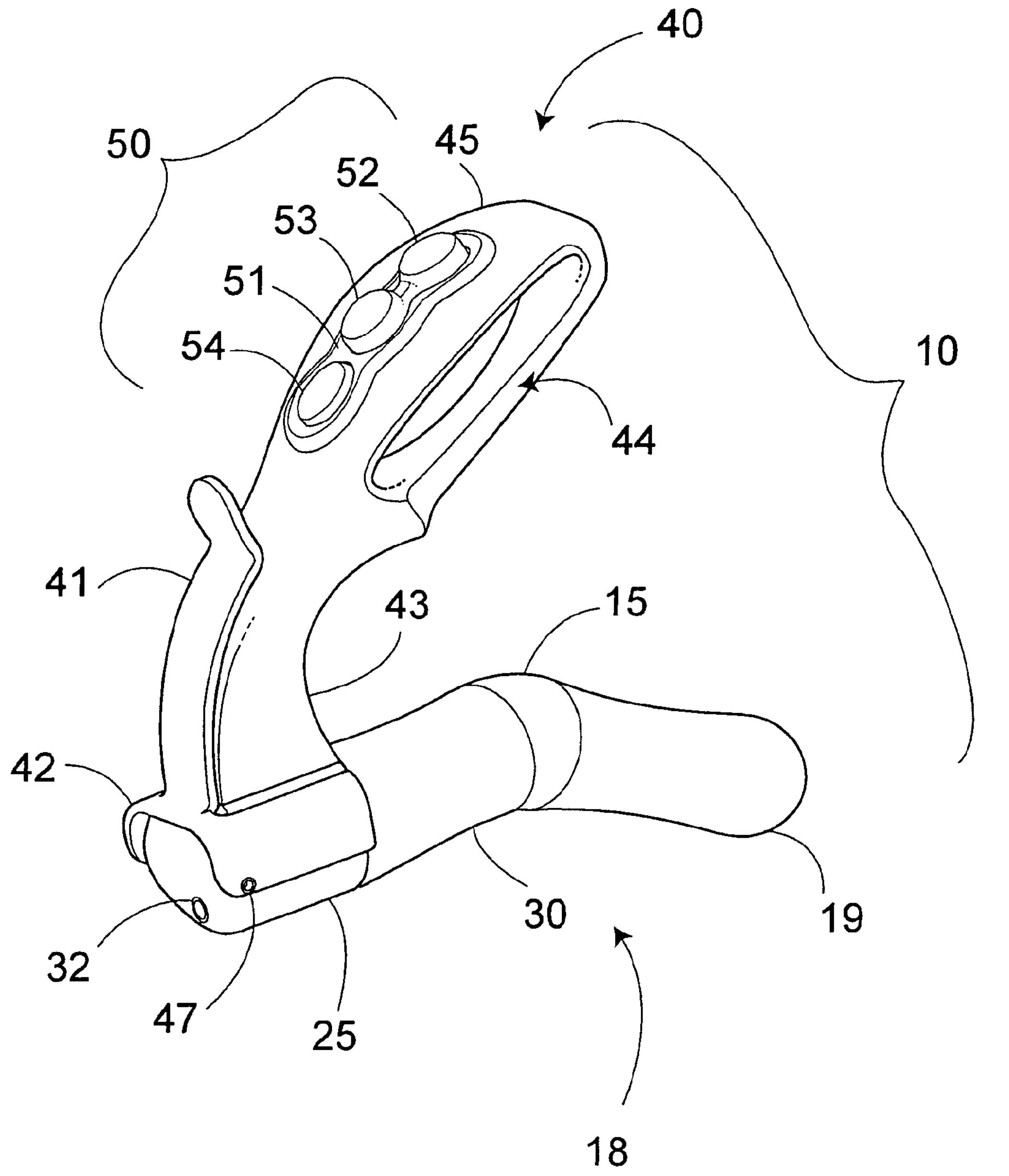
FIG. 2 is a perspective view of the embodiment from FIG. 1 showing the dildo portion rotated into a downward-extending orientation.
Figure 3:
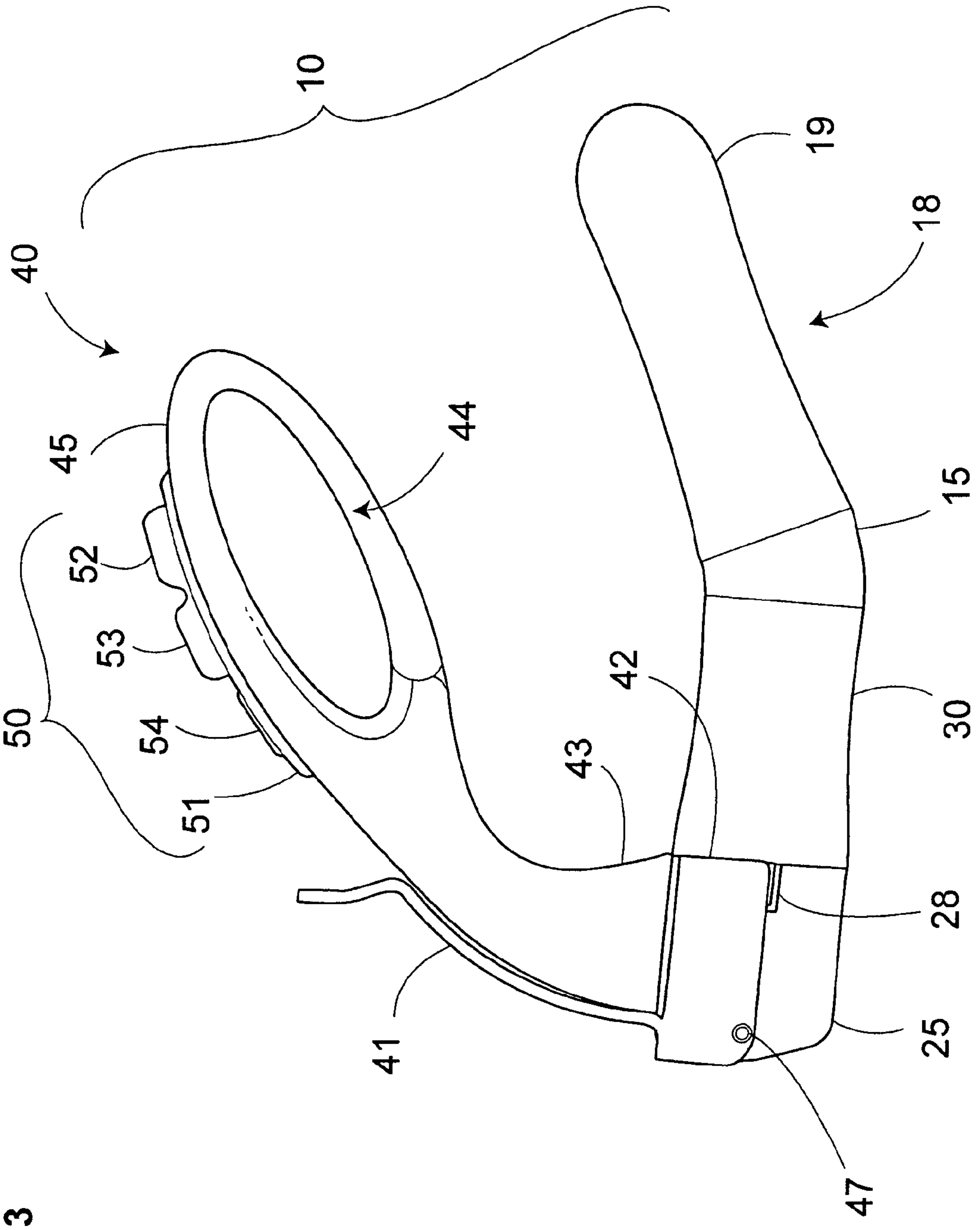
FIG. 3 is a side view of the embodiment shown in FIG. 1.

As is best seen in FIGS. 1-3 and 6, the vertical handle member 43 extends generally upward from handle end cap structure 25, to which it is integrally conjoined, and then cantilevers outward into a toroidal loop structure 44 configured to slidingly accept a hand therethrough as shown in FIG. 4(*a*). The dimensions and topography of the toroidal loop 44 are configured to facilitate secure grasping and gripping by hand. It is preferred that the lower portion of the toroidal loop 44 has a narrower width than the upper portion in order facilitate secure grasping and gripping by hand of the lower portion of the toroidal loop 44. This preferred form is particularly useful for low quadriplegics having permanently curled fingers because this configuration of bottom edge of the toroidal loop 44 may be gently forced into the space between the curled fingers and palm thereby enabling users with curled fingers to get a purchase on the thinner lower portion of the toroidal loop 44 after which, the handle component can be rotated so that the upper portion of the toroidal loop is superposed over the top of the user's hand as shown in FIG. 4(*a*)—otherwise they would have to force their hands into the aperture portion of the toroidal loop 44 with bent fingers, knuckle first. The vibrostimulation device 10 may then be maneuvered by the user into various positions as exemplified in FIGS. 4(*b*) and 5, and then manipulated as desired.

The switching device 50 comprises a pliable resilient housing 51 containing therein a plurality of switches, each communicating with a dedicated compressible button for controlling therewith the operation of motor 21 housed within the vibrating end portion 19. By way of example in reference to FIGS. 1-3, button 54 may operate a first switch to turn the motor 21 on and off, whereas button 53 may operate a second switch for increasing and decreasing the amplitude of the vibratory motions generated by the motor 21, where as button 52 may operate a third switch for increasing and decreasing the oscillating and resonating intensity of the vibrations produced by the motor 21. It is preferred that switches 52, 53 and 54 are a pushbutton type. It is further preferred that the dimensions and architecture of the switching device 50 are configured to facilitate their handling and manipulation by individuals with impaired motor control and/or impaired tactile sensory perception, simply by applying pressure to one or more of the switches 52, 53, and 54 with the heel of a thumb or the heel or side of a palm, thereby enabling satisfactory manipulation and operation of the vibrostimulation device 10 while in use for example, as illustrated in FIGS. 4 and 5(*b*).

It is preferred that the handle component 40 comprises a somewhat stiff yet pliable and resilient material as exemplified by rubber, polyurethane, polyurethane rubber, foamed polyurethane, flexible epoxy, elastomer and the like. However, it is preferable that materials selected to comprise the handle component 40 are durable, scratch-resistance and impenetrable by moisture and fluids. Alternatively, the vertical member 43 and toroidal loop structure 44 of the handle component 40 may comprise a metal or hard plastic material that is sealingly overlaid with a soft, compressible moisture-impenetrable elastomeric material.

Figure 1:
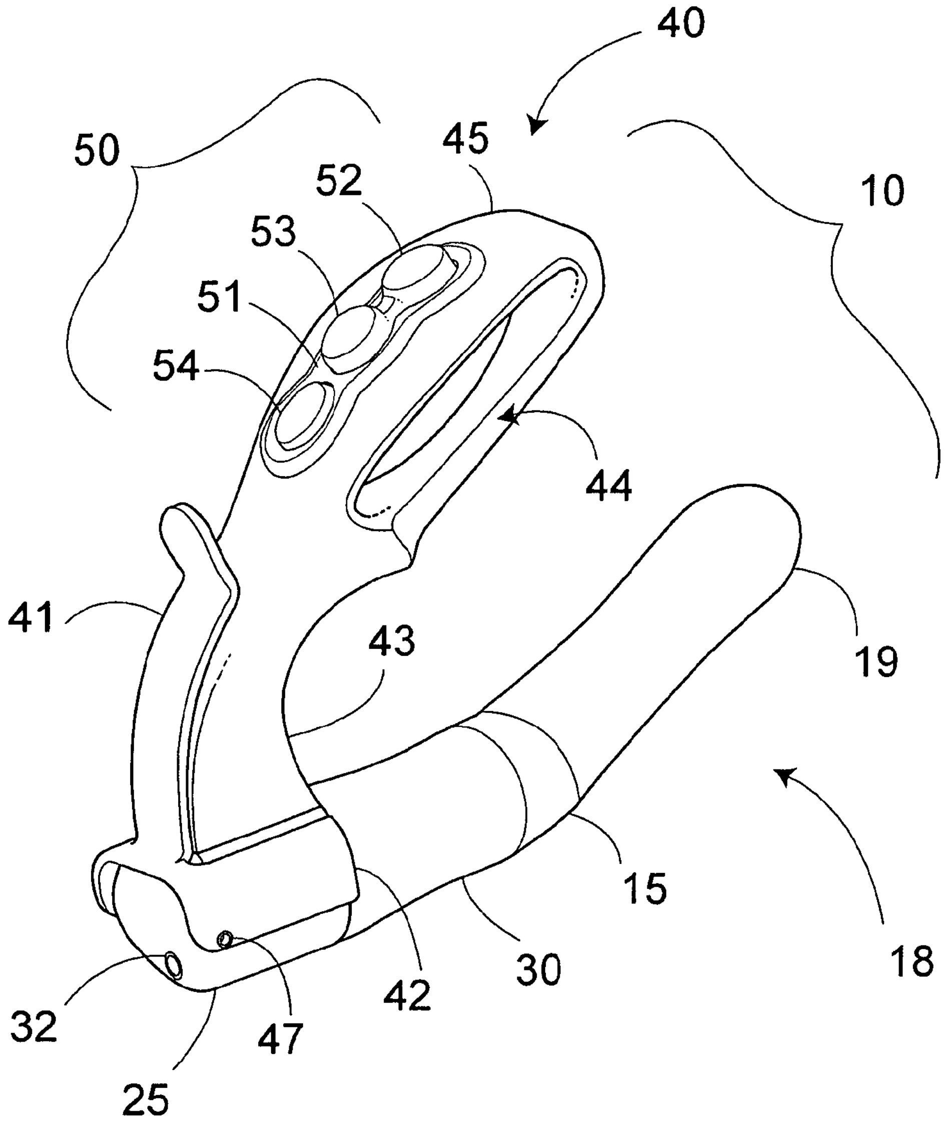
FIG. 1 is a perspective view of a preferred embodiment of the present invention showing the dildo portion rotated into an upward-extending orientation.

The handle component 40 is preferably provided with a locking device as exemplified in FIGS. 1-3, 6 and 7 by a locking lever 41 that is contoured to fit against the adjacent vertical handle member 43 topography, and is pivotably connected to the handle end cap structure 25 by a pin 47 inserted through bores provided therefore. The locking lever 41 is provided with a pair of opposing inwardly biasing flaps 42 configured to slidingly communicate with the pair of arms 26 and their lobed ends 27 provided on the handle end cap structure 25. Moving the locking lever 21 from an unlocked position as shown in FIG. 6 to a locked position as shown in FIG. 3 causes the flaps 42 to compressingly engage the lobes 27 of the arms 26 thereby forcing each lobe 27 into the space interposed two adjacent ribs 36 of the sprocket barrel end cap structure 34 underneath the lobe 27, while at the same time, the locking lever 41 is abuttingly communicating with the vertical handle member 43. Pulling back on the locking lever 41 causes it to pivot about pin 47 thereby disengaging flaps 42 from the lobes 27 of the arms 26. When the locking lever 41 is in the unlocked position as shown in FIG. 7, the vibrator module can be rotated 360° within the handle end cap structure 25 to desired positions relative to the handle component 40, for example as shown in FIG. 1 with the dildo end extending upward toward the toroidal loop 41 portion of the handle component 40, and alternatively as shown in FIG. 2, with the dildo end extending downward and away from the handle component 40. Accordingly, it is possible to tailor the dildo and handle configuration to accommodate a user's body shape and size, their abilities to manipulate and maneuver the device, and their preferences for use the vibrostimulation device 10 in sitting and/or reclining positions.

Figure 19:
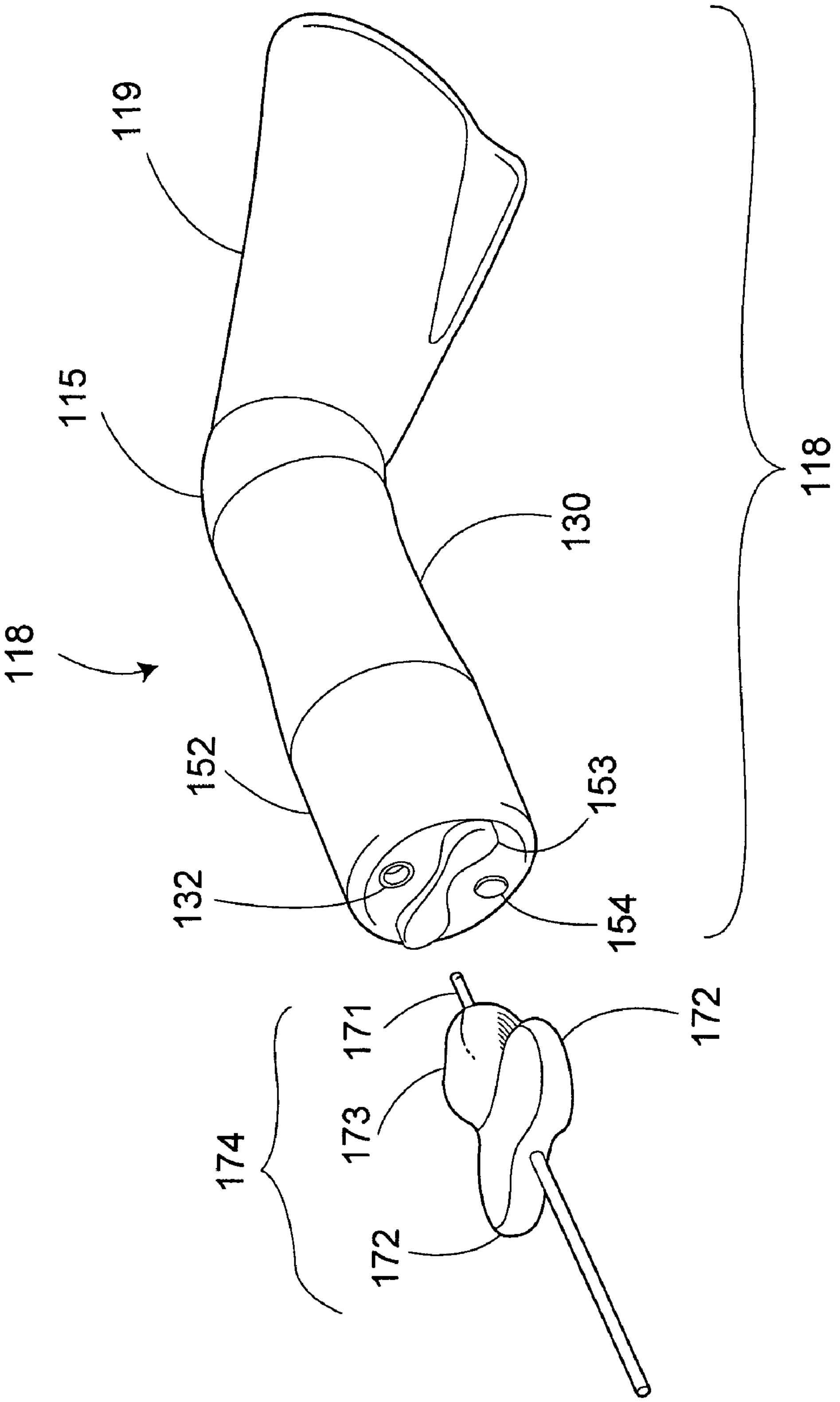
FIG. 19 is a perspective view showing the vibrator module of the present invention provided with an end cap structure configured to enable use of the vibrator module exclusive of the handle component.

The handle base portion 25 is provided with a receptacle 32 configured for communicating and cooperating with an electrical charging jack 174, as is best seen in FIG. 19. When the electrical charging jack 174 is inserted in to the receptacle 32, it communicates with the rechargeable battery pack 31 via the electrical switching contact plate 35*a* and the electrical contact plate 35*b*.

Figure 12:
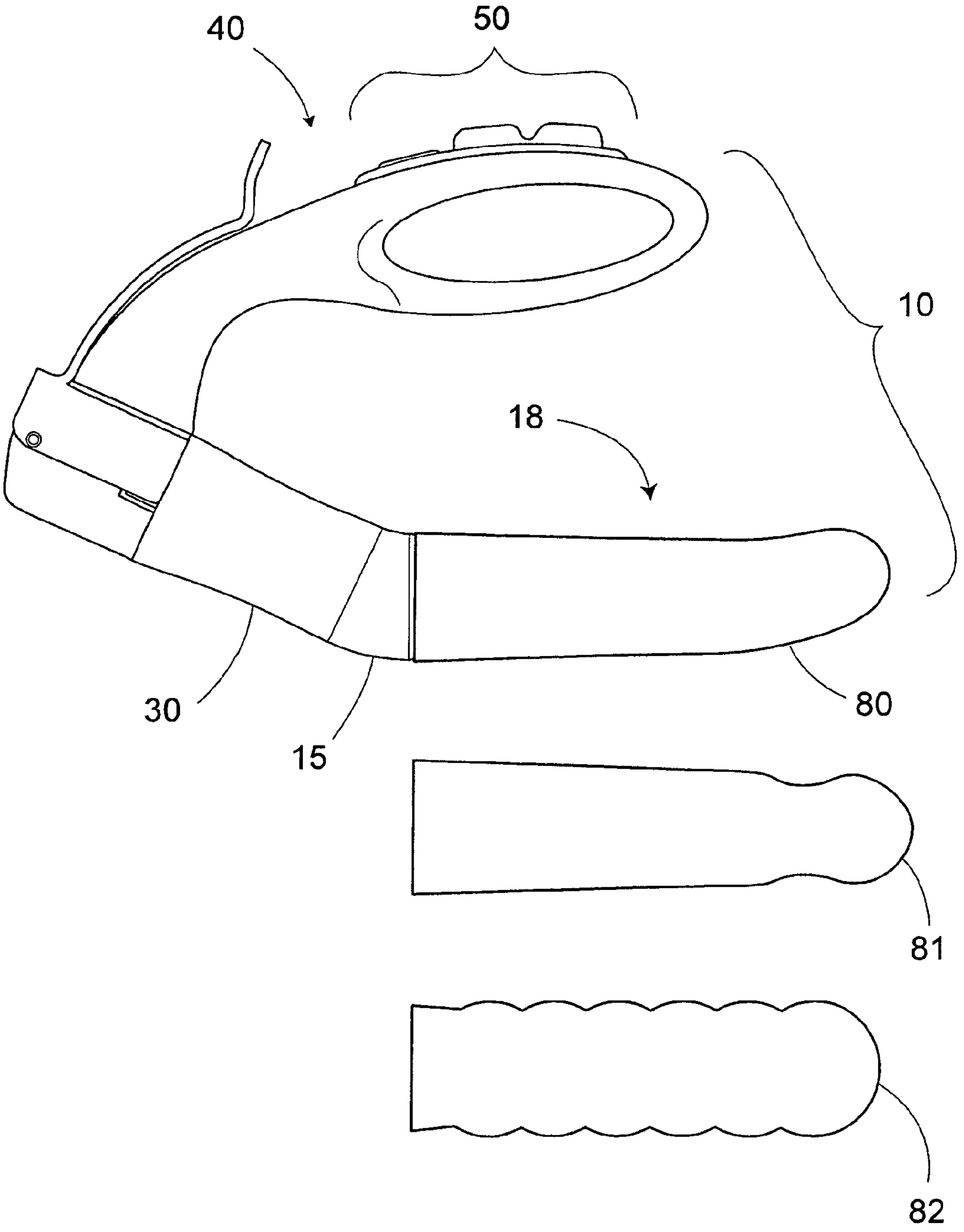
FIG. 12 is a side view of the embodiment from FIG. 1 shown with alternative configurations for the dildo portion.

Those skilled in these arts will understand that the nature and quality of the vibrostimulation provided by the device 10 of the present invention can be modified by simply slipping textured condoms over the dildo portion 19 of the vibrator module 18, or alternatively, by providing various molded dildo configurations as exemplified in FIG. 12 by dildo ends 80, 81 and 82. Those skilled in these arts will also understand that the nature, quality and intensity of vibrostimulation provided by device 10 can be modified by the type of motor and eccentric weight selected for installation into the dildo portion 19, and/or by the shaft assembly configuration selected to mount the eccentric weight onto the motor.

FIGS. 13-20 illustrate another preferred embodiment of the present invention configured for sliding communication with and along body surfaces and external sex organs such as penises and breasts.

As can best be seen in FIGS. 13-16, the device 110 is provided with vibrator module 118 comprising a vibrating end portion 119, a power supply module 130, a shock-absorbing coupler 115 interconnecting the proximal end of the vibrating end portion 119 and the distal end of the power supply module 130, a handle component 140 cooperating with the proximal end of the power supply module 130 and a switching device 150 for electrically controlling the vibrator module 118. It is to be noted that the coupler 115 and power supply module 130 of the device 110 exemplified in FIGS. 13-20 are identical to the coupler 15 and power supply module 30 of the device 10 exemplified in FIGS. 1-12. The handle component 140 of device 110 comprises an elongate base saddle section 144 having a longitudinal axis, said saddle 144 having a proximal end superposable over the proximal end of the power supply module 30 and a distal end superposable approximate the distal end of the power supply module 30. The saddle 144 is provided with a pair of opposing downward extending flanges 145 along the saddle's longitudinal axis, said flanges 145 configured to releasably engage the proximal end of the power supply module 130. The proximal ends of the opposing flanges 145 are pivotably connected by a pin 147 to a handle end cap structure 125 that is configured for slidingly receiving and releasably engaging therein the proximal end of the power supply housing 130. The handle component 140 further comprises a generally vertical portion 143 extending upwards from the proximal end of the handle saddle 144, said vertical portion 143 cantilevered into a curvilinear elongate top handle portion 141 that extends backward beyond the proximal end of the handle saddle 144 to a downward-hooking terminus 142.

A preferred embodiment for the vibrating end portion 119 of the vibrator module 118 is best seen in FIGS. 13-16, said end portion 119 configured for sliding communication about and along body surfaces and external sex organs. The vibrating end portion 119 generally comprises a truncated cone provided with a distal end 120 that is provided with backward depending acute angle selected from the range of 25° to 85° and most preferably from the range of 45° to 65°. The distal end of the vibrating end portion may be furthered provided with a flanged area terminating at the distal end 120. Alternative, the vibrating end portion may comprise a truncated cylinder (not shown). The distal end 120 is preferably provided with a concave surface 121 configured for sliding communication with external body parts such as the penis glans, scrotum, clitoris and/or nipples. An elongate wedge-shaped rib 124 may be optionally provided along the longitudinal axis of the vibrating end portion 119. It is preferable that the elongate rib 124 depends from and extends outward from the proximal end of the vibrating end portion 119 to conjoin the distal end 120 at its closest point to the proximal end of the vibrating end portion 119, said elongate rib 124 providing an anvil-shaped profile to the distal end 120. The elongate rib 124 is preferably conjoined to the vibrating end portion 119 by opposing concave surfaces 123, said concave surfaces 123 useful for sliding communication with a penile shaft. Those skilled in these arts will understand that the entire outer surface of the vibrating end portion 119 may be used for sliding communication with various portions and regions of a male's or a female's body surfaces for tactile stimulation of deep-phasic pressure-sensitive receptors distributed throughout subcutaneous regions of the body.

Figure 17:
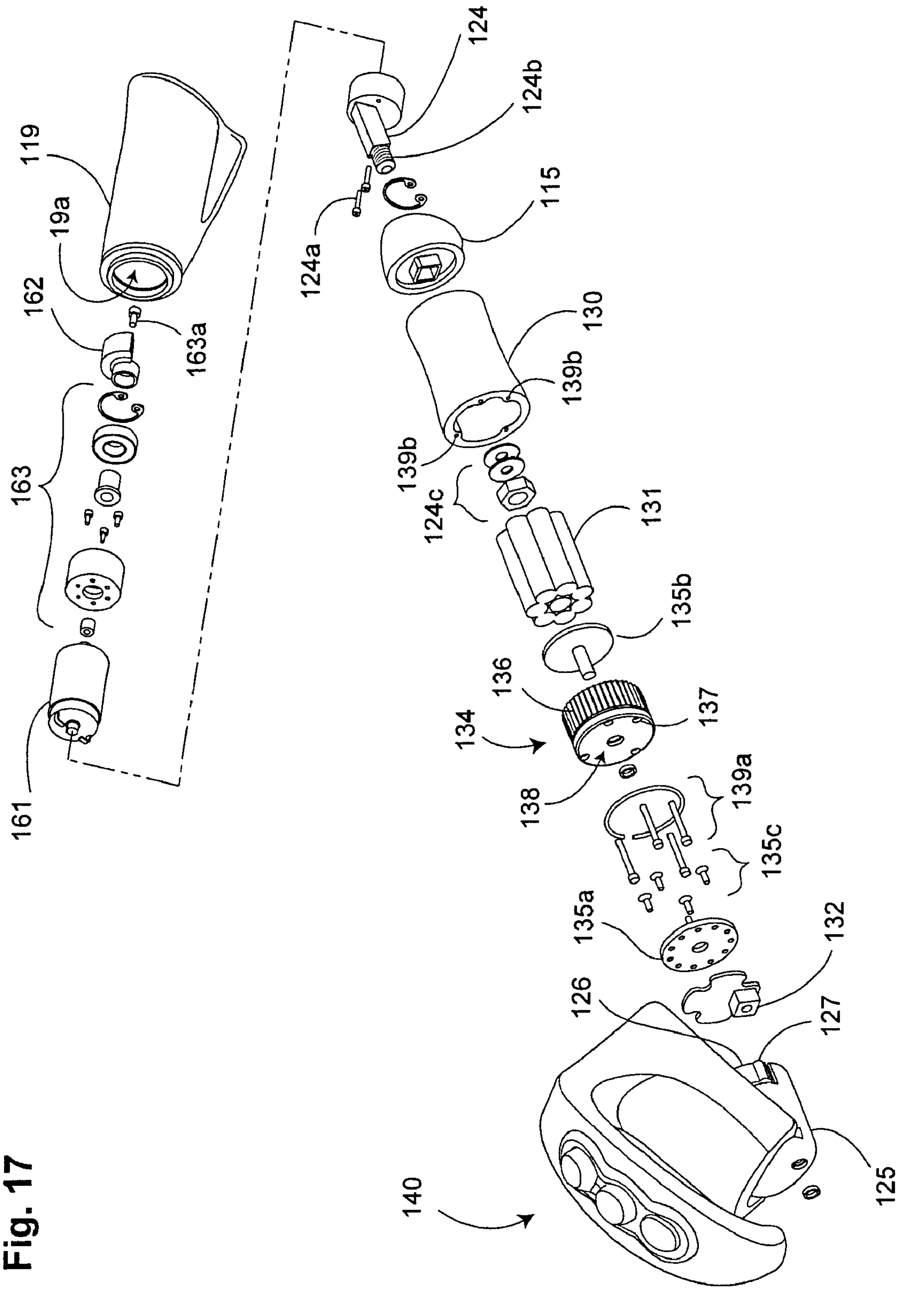
FIG. 17 is an exploded perspective view of the embodiment shown in FIG. 14.

As shown in FIGS. 17 and 19, the vibrating end portion 119 is provided with a bore **119*a* extending inward from the proximal end of the vibrating end portion 119. The bore 119*a* is configured to securely house the motor 161, eccentric weight 162 and the shaft assembly 163 interconnecting the motor 161 and eccentric weight 163. A plurality of O-rings (not shown) may be provided for encircling the motor 161 to space apart the motor 161 from the bore 119*a* thereby resulting in heat sequestration and dissipation from the outer surfaces of the vibrating end portion 119**.

The vibrating end portion 119 is securely mounted to the coupler 115 with screws **124*a*, and communicates with the power supply module 130 via wiring conduit structure 124 that is secured to the distal end of the power module 130 with a nut and washer set 124*c* threadably engaged with the threaded end 124*b* of the wiring conduit structure 124. The power module 130 is configured to partially house a battery pack 131 so that the electrical discharge end of the battery pack communicates with the wiring conduit structure 124. The power module 130 is provided with a sprocket barrel end cap structure 134 configured to house therein the portion of the battery pack 131 extending from the power module 130. The sprocket barrel end cap structure 134 is securely mounted to the power module 130 by bolts 139*a* extending through bores 137 in the end wall 138 of the sprocket barrel end cap structure 134, said bolts 139*a* cooperating with threaded bores 139*b* provided in the proximal end of the power module 130. An electrical contact plate 135*b* provided with an integral conduit extending therefrom, is interposed the battery pack 131 and the end wall 318 of the sprocket barrel end cap structure 134, said electrical contact plate 135*b* communicating therethrough said sprocket barrel end cap structure 134 with a second electrical switching contact plate 135*a*.**

Figure 18A:
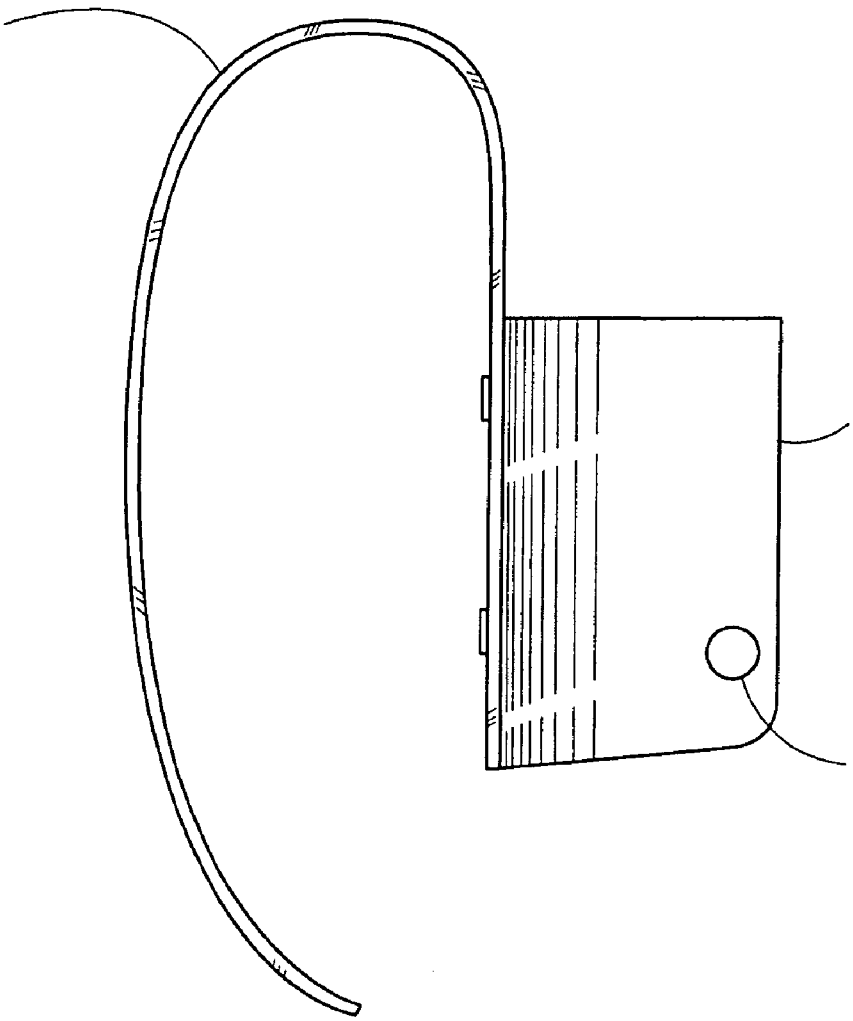
FIG. 18(*a*) is a cross-sectional view of the metal framework for the handle component of the embodiment shown in FIG. 14.
Figure 18B:
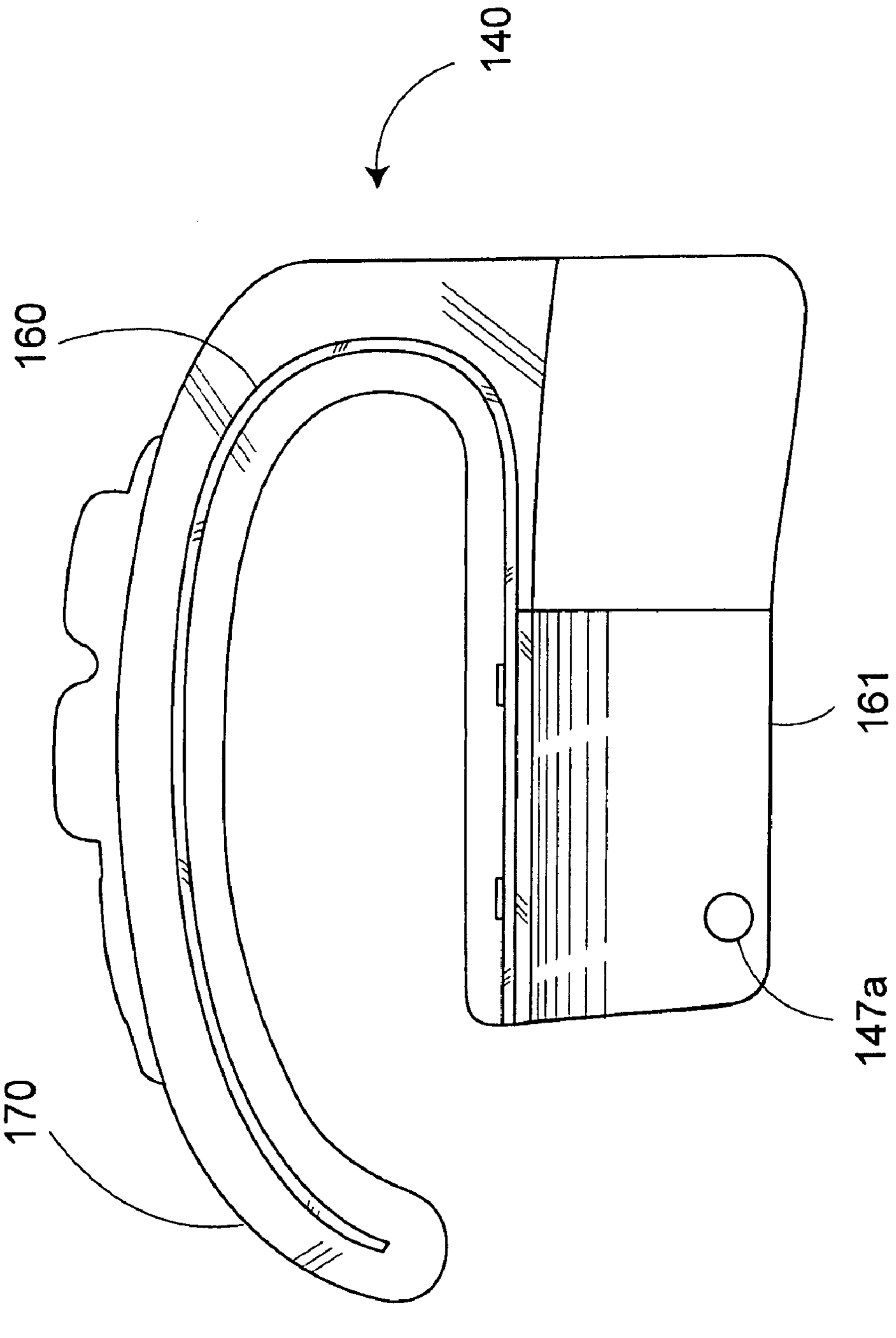

As shown in FIGS. 15-18, the handle end cap structure 125 comprises a housing provided with a cylindrical inner bore configured to slidingly receive therein the sprocket barrel end cap structure 134 that is mounted to the proximal end of the power supply module 130. As shown in FIG. 17, a power jack receptacle 132 and an electrical switching plate **135*a* are interposed the handle end cap structure 125 and the sprocket barrel end cap structure 134. The sprocket barrel end cap structure receiving end of the handle end cap structure 125 is provided with a pair of opposed L-channels 128 that define a pair of inwardly-biasing arms 126, each arm 126 provided with a lobed end 127. As is best seen in FIGS. 18**(*a*) and (*b*), the handle component 140 is provided with a elongate curvilinear biasing metal framework comprising a curvilinear biasing rib 160 interconnected with a metal U-shaped channel 161, said rib 160 and channel 161 together defining the handle saddle 144, flanges 145 extending downward from the saddle 144, the upward extending vertical portion 143, and the cantilevered curvilinear elongate top handle portion 141 extending backward from the vertical portion 143. The U-shaped channel is provided with opposing bores **147*a* for pivotably connecting the handle flanges 145 to the handle end cap structure 125. The metal framework comprising rib 160 and channel 161 is preferably embedded in and overlaid with a somewhat stiff yet pliable and resilient material 170 as exemplified by rubber, polyurethane, polyurethane rubber, foamed polyurethane, flexible epoxy, elastomer and the like. However, it is preferable that materials selected to comprise the handle component 140** are durable, scratch-resistance and impenetrable by moisture and fluids.

Figure 13:
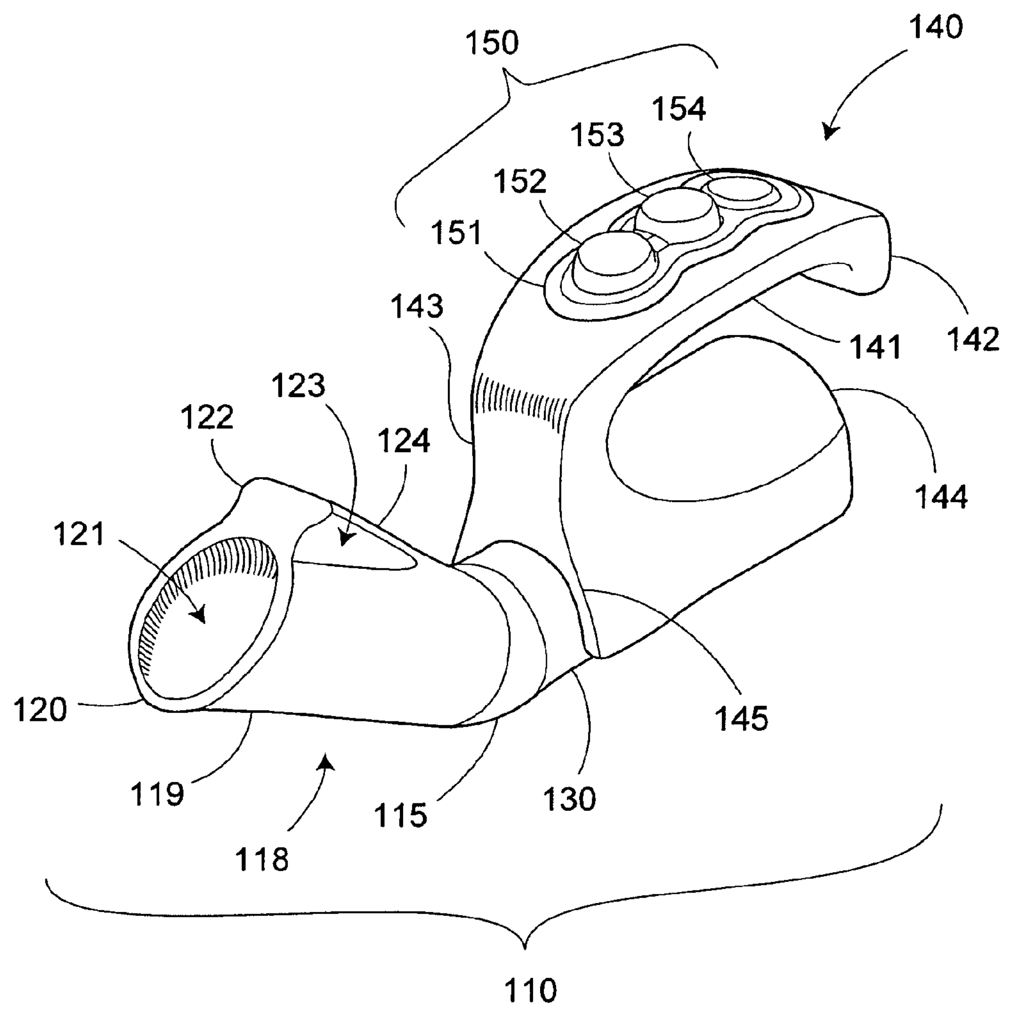
FIG. 13 is a perspective view of another preferred embodiment of the present invention showing the vibrostimulator portion rotated into an upward-extending orientation.
Figure 14:
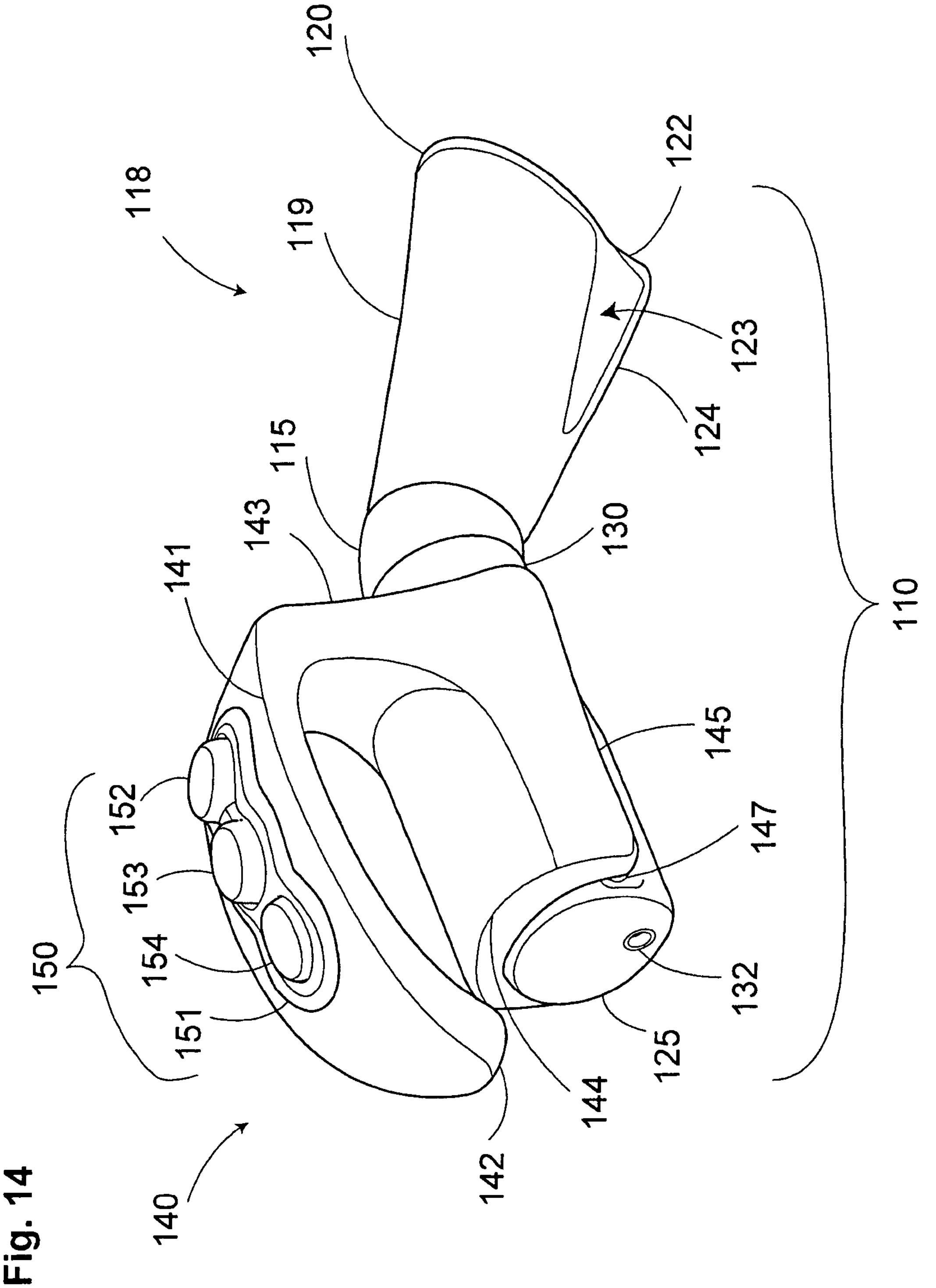
FIG. 14 is a perspective view of the embodiment from FIG. 13 showing the vibrostimulator portion rotated into a downward-extending orientation.
Figure 15:
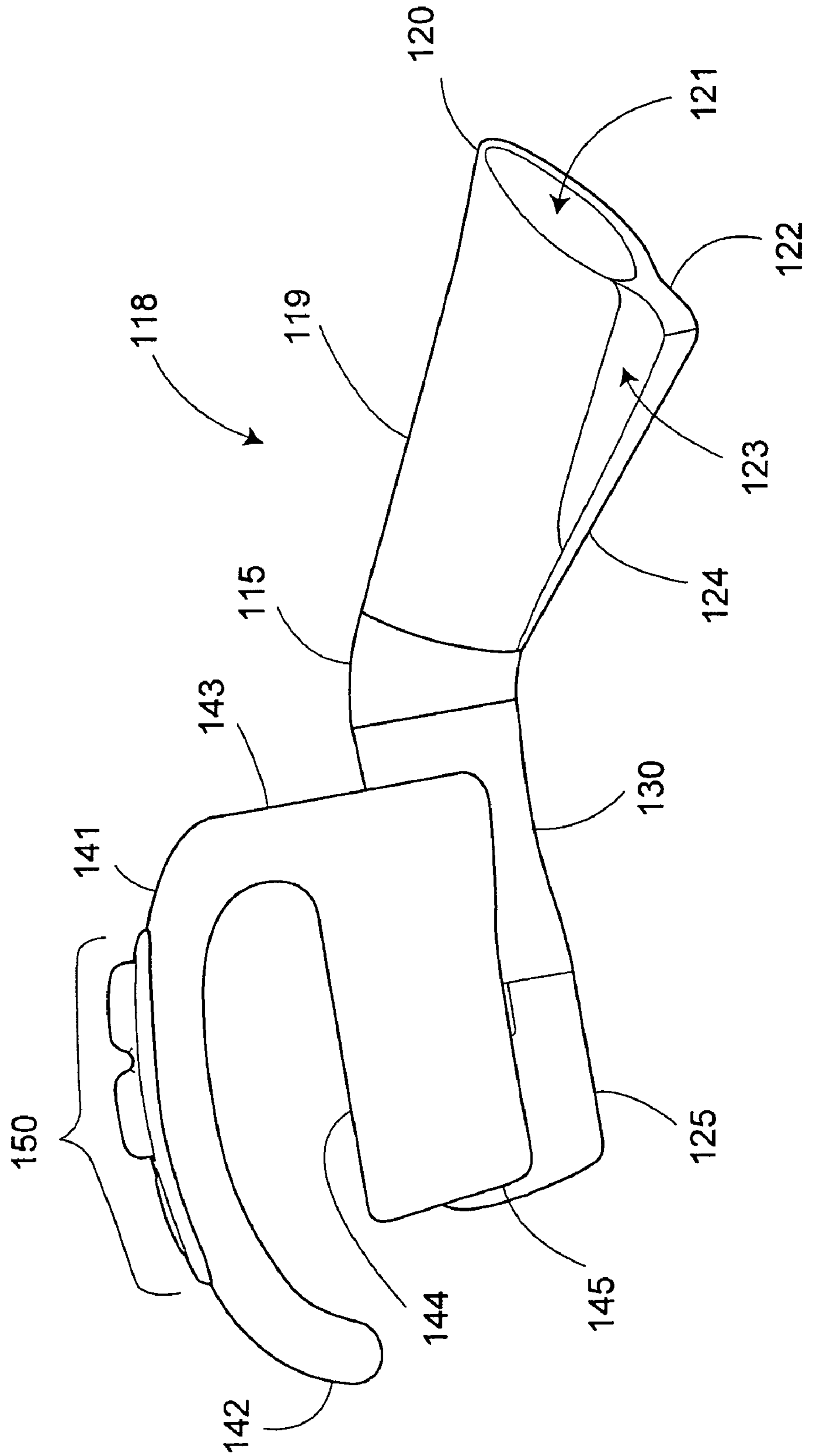
FIG. 15 is a side view of the embodiment shown in FIG. 14 wherein the vibrostimulator portion has been partially rotated sideways.
Figure 16:
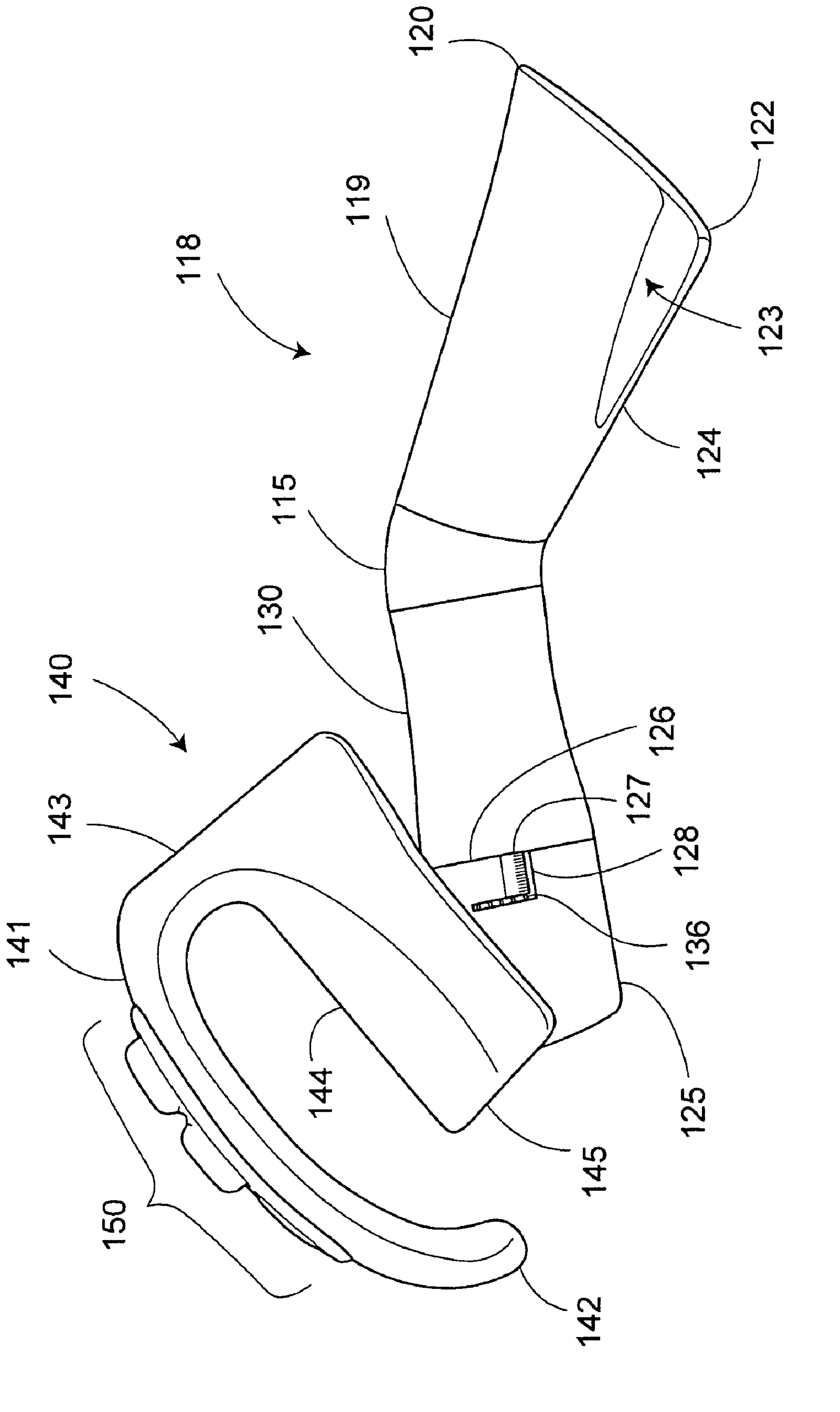
FIG. 16 is a side view of the embodiment from FIG. 14 wherein a locking device is shown in a disengaged position to enable rotatable reorientation of the vibrostimulator portion.

As shown in FIGS. 15-17, the outer surface of the sprocket barrel end cap structure 134 is preferably provided with a contiguous plurality of paired ribs 136 extending along the longitudinal axis of sprocket barrel end cap structure 134, said contiguous plurality of ribs 136 encircling the sprocket barrel end cap structure 134. When the sprocket barrel end cap structure 134 is inserted into the handle end cap structure 125, each lobed end 127 of each inwardly biasing arm 126 of the handle end cap structure 125 will communicate with and engage the space interposed two adjacent ribs 136 on the outer surface of the sprocket barrel end cap structure 134, thereby enabling precisely controllable rotation of the vibrator module 118 within the handle end cap structure 125. When the handle component 140 is pivotably moved from a disengaged position with the vibrator module 118 as illustrated in FIG. 16, to an engaged position as illustrated in FIG. 15, the biasing U-shaped channel 161 portion of the metal framework defining the flanges 145 extending downward from the saddle 144, will compressingly engage the lobes 127 of the arms 126 thereby forcing each lobe 127 into the space interposed two adjacent ribs 136 of the sprocket barrel end cap structure 134 underneath the lobe 127, while at the same time, the inner surface of the saddle 144 abuttingly communicates with upper surface regions of the handle end cap structure 125 and the power supply module 130. Therefore, pulling back on the top handle portion 141 will disengage the flanges 145 from the lobes 127 of the arms 126. When the handle component 140 is in the unlocked position as shown in FIG. 16, the vibrator module 118 can be rotated 360° within the handle end cap structure 25 to desired positions relative to the handle component 140, for example as shown in FIG. 13 with the vibrating end portion 119 extending upward toward, and alternatively as shown in FIG. 14, with the vibrating end portion 119 extending downward. Accordingly, it is possible to tailor the configuration of the vibrating end portion 119 and handle component 140 to accommodate a user's body shape and size, their abilities to manipulate and maneuver the device, and their preferences for use the vibrostimulation device 110 in sitting and/or reclining positions.

As is best seen in FIG. 15, the open-ended design of the handle component 140 enables a user with limited control over or lack of dexterity in controlling the cooperation between their fingers, thumbs, palms and wrists, are able to slip a hand into the aperture defined by the handle saddle 144 and the cantilevered curvilinear elongate top handle portion 141 so that the bottom surface of their palm contacts the handle saddle 144 or alternatively, the top handle portion 141. The downward-hooking terminus 142 of the handle portion serves to retain the user's hand within handle aperture area defined by the saddle 144 and the top handle portion 141 even if the user is not able to apply a gripping pressure to the saddle 144 or to the top handle portion 141.

It is preferred that the top surface of top handle portion 141 is configured to receive therein an easily manipulable electrical switching device 150 comprising an on/off switch 154, a first switch 152 configured for increasing the frequency of the vibrations, and a second switch 153 configured for decreasing the frequency of the vibrations, said switches covered by a pliable resilient material. It is preferred that switches 152, 153 and 154 are a pushbutton type. It is further preferred that the dimensions and architecture of the switching device 150 are configured to facilitate their handling and manipulation by individuals with impaired motor control and/or impaired tactile sensory perception, simply by applying pressure to one or more of the switches 152, 153, and 154 with the heel of a thumb or the heel or side of a palm, thereby enabling satisfactory manipulation and operation of the vibrostimulation device 110 while in use.

Another preferred embodiment of the present invention is illustrated in FIG. 19 wherein the vibrostimulation device 110 is provided with a recharging apparatus comprising a transformer (not shown) for demountably engaging an electrical outlet, said transformer interconnected with wiring to a male charging jack 171 configured to slidingly communicate with receptacle 132 for charging rechargeable battery pack 131 contained within power supply module 131. The male charging jack 171 is integrally encased within a central rib portion 173 of a graspable housing 174 provided with wing-shaped paddles 172 extending therefrom central rib portion 173, said wing-shaped paddles 172 having a thinner cross-sectional profile relative to central rib portion 173. Consequently, when the graspable housing 174 is resting on a flat surface, one of wing-shaped paddles 172 is elevated above the horizontal surface thereby providing a graspable profile for persons with limited motor control capability to securely grip and manipulate housing 174. It is to be noted that the end profile of central rib portion 173 is configured to slidingly communicate and mate with concave end 132 of the power supply module 130 thereby facilitating insertion of male charging jack 171 into receptacle 132. It is to be further noted that the configuration of graspable housing 174 and the male charging jack 171 facilitates slidingly communication and mating with the receptacle 32 of the preferred embodiment for the handle component 40 illustrated in FIGS. 1-12.

It is to be noted that the vibrator modules of the present invention as exemplified by the vibrator module 18 in FIGS. 1-12 and vibrator module 118 in FIGS. 13-17, can be optionally provided with a housing 152 configured to receive therein, and communicate and cooperate therewith the sprocket barrel end cap structures 34 and 134 respectively, to enable use of the vibrator modules when they are detached from the handle components 40 and 140 respectively. The housing 152 is preferably provided with an pushbutton on/off switch 154 and a rocker switch 153 for increasing and decreasing the speed and or intensity of vibrations produced at the vibrating ends of the vibrator modules.

While this invention has been described with respect to the preferred embodiments, it is to be understood that various alterations and modifications can be made to the various modules and components of the user-friendly vibrostimulation device within the scope of this invention.

What is claimed is:

1. A vibrostimulation device configured for slidingly communicating with tactile receptors in a human body, said device comprising:

an elongate vibrator module provided with a vibrating end portion containing therein an electrically controllable vibratory apparatus and a power supply module configured for communication with a switching device for controlling said vibratory device, the proximal end of said vibrating end portion and the distal end of said power supply module interconnected by a shock-absorbing coupler; and a handle component configured to releasingly engage and rotationally communicate with the proximal end of said power supply module.

2. The vibrostimulation device of claim 1 wherein said shock-absorbing coupler is configured to extend said vibrating end portion away from said handle component at an acute angle.

3. The vibrostimulation device of claim 2 wherein said shock-absorbing coupler is configured to extend said vibrating end portion away from said handle component at an acute angle selected from the range of 5° to 65°.

4. The vibrostimulation device of claim 1 wherein said shock-absorbing coupler is configured to extend said vibrating end portion away from said handle component at an acute angle selected from the range of 20° to 30°.

5. The vibrostimulation device of claim 1 wherein said shock-absorbing coupler comprises a resilient material.

6. The vibrostimulation device of claim 5 wherein said shock-absorbing coupler comprises a resilient material selected from the group comprising rubber, polyurethane, polyurethane rubber, foamed polyurethane, flexible epoxy, and elastomer.

7. The vibrostimulation device of claim 1 wherein said vibrating end portion containing therein an electrically controllable vibratory apparatus is provided with an insulator interposed said vibrating end portion and said vibratory apparatus.

8. The vibrostimulation device of claim 1 wherein said insulator comprises a plurality of spaced apart resilient rings.

9. The vibrostimulation device of claim 1 wherein the proximal end of said power supply module is provided with a cylindrical end cap structure extending along a longitudinal axis, said end cap structure having a plurality of ribs extending outward from and spaced about the outer surface of said end cap structure, said ribs extending therealong the longitudinal axis, said end cap structure configured for releasable engagement and rotational communication with said handle component.

10. The vibrostimulation device of claim 9 wherein said plurality of ribs is contiguous.

11. The vibrostimulation device of claim 9 wherein said end cap structure is provided with a switching device configured for controlling said vibratory device.

12. The vibrostimulation device of claim 1 wherein said vibrating end portion comprises an elongate cylindrical shaft.

13. The vibrostimulation device of claim 12 wherein said elongate cylindrical shaft is integrally provided with a decorative profile.

14. The vibrostimulation device of claim 13 wherein said decorative profile is annularly spaced along said cylindrical shaft.

15. The vibrostimulation device of claim 12 wherein the distal end of the elongate cylindrical shaft is truncated.

16. The vibrostimulation device of claim 15 wherein said truncated end is provided with a concave surface.

17. The vibrostimulation device of claim 15 wherein said truncated cylindrical shaft is provided with an elongate web depending from the proximal end of said shaft, said web provided with concave opposing surfaces.

18. The vibrostimulation device of claim 1 wherein the handle component comprises a curvilinear upper portion cantilevered from a vertical portion pivotably connected to a base portion, said base portion configured for releasably engaging and rotationally communicating with said vibrator module.

19. The vibrostimulation device of claim 18 wherein said handle base portion is configured to releasably engage said elongate ribs provided thereon the vibrator module end cap structure.

20. The vibrostimulation device of claim 18 wherein said handle top portion is configured to receive therein a switching device configured to control said vibratory apparatus, said switching device cooperating with said handle base portion for communicating therewith said vibrator module.

21. The vibrostimulation device of claim 18 wherein said handle upper portion comprises a graspable toroidal loop configured to receive a hand thereabout.

22. The vibrostimulation device of claim 18 wherein said handle upper portion is provided with a hook-shaped terminus, said terminus depending toward said handle base portion.

23. The vibrostimulation device of claim 18 wherein said handle component comprises a compressible resilient material.

24. The vibrostimulation device of claim 18 wherein said resilient material is selected from the group comprising rubber, polyurethane, polyurethane rubber, foamed polyurethane, flexible epoxy, and elastomer.

25. The vibrostimulation device of claim 23 wherein said handle component comprises a compressible resilient material overlaid onto and cooperating with a biasing metal framework.

26. A kit of parts forming a vibrostimulation device configured for slidingly communicating with tactile receptors in a human body, the kit comprising at least an elongate vibrator module provided with a vibrating end portion containing therein an electrically controllable vibratory apparatus and a power supply module configured for communication with a switching device for controlling said vibratory device, the proximal end of said vibrating end portion and the distal end of said power supply module interconnected by a shock-absorbing coupler, and a handle component configured to releasingly engage and rotationally communicate with the proximal end of said power supply module.

27. The kit of parts of claim 26, including instructions for assembly of the parts to form a vibrostimulation device.

28. The kit of parts of claim 26, wherein the distal end of said vibrating end portion of said vibrator module is truncated.

29. The kit of parts of claim 28, wherein said truncated end is provided with a concave surface.

30. The kit of parts of claim 26, wherein said vibrating end portion of said vibrator module is provided with an elongate web depending from the proximal end to approximate the distal end of said vibrating end portion, said web provided with concave opposing surfaces.

* * * * *